United States Patent
Shin et al.

(10) Patent No.: US 9,204,840 B2
(45) Date of Patent: Dec. 8, 2015

(54) REAL TIME SELF-ADJUSTING CALIBRATION ALGORITHM

(75) Inventors: John J. Shin, LaCanada, CA (US); Nandita N. Patel, Los Angeles, CA (US); Sami Kanderian, Jr., Northridge, CA (US); Lu Wang, Pasadena, CA (US); Richard Yoon, Northridge, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 1772 days.

(21) Appl. No.: 12/179,536

(22) Filed: Jul. 24, 2008

(65) Prior Publication Data

US 2009/0005666 A1 Jan. 1, 2009

Related U.S. Application Data

(60) Division of application No. 10/750,978, filed on Dec. 31, 2003, now Pat. No. 7,890,295, which is a continuation-in-part of application No. 10/141,375, filed on May 8, 2002, now Pat. No. 6,895,263, which is a continuation-in-part of application No. 09/511,580, filed on Feb. 23, 2000, now Pat. No. 6,424,847.

(51) Int. Cl.
*G01N 33/48* (2006.01)
*G01N 31/00* (2006.01)
(Continued)

(52) U.S. Cl.
CPC ............. *A61B 5/6849* (2013.01); *A61B 5/1495* (2013.01); *A61B 5/14532* (2013.01);
(Continued)

(58) Field of Classification Search
CPC . H03H 21/0012; H03H 21/0029; G06T 5/002
See application file for complete search history.

(56) References Cited

U.S. PATENT DOCUMENTS

| 4,562,751 A | 1/1986 | Nason et al. |
| 4,573,994 A | 3/1986 | Fischell et al. |

(Continued)

FOREIGN PATENT DOCUMENTS

| JP | 11-173836 A | 7/1999 |
| JP | 2001-091466 A | 4/2001 |

(Continued)

OTHER PUBLICATIONS

Parker et al. (IEEE Transactions on Biomedical Engineering, 1999, 46(2), 148-157).*

(Continued)

*Primary Examiner* — Larry D Riggs, II
(74) *Attorney, Agent, or Firm* — Berkeley Law & Technology Group, LLP

(57) ABSTRACT

A method of calibrating glucose monitor data includes collecting the glucose monitor data over a period of time at predetermined intervals. It also includes obtaining at least two reference glucose values from a reference source that temporally correspond with the glucose monitor data obtained at the predetermined intervals. Also included is calculating the calibration characteristics using the reference glucose values and corresponding glucose monitor data to regress the obtained glucose monitor data. And, calibrating the obtained glucose monitor data using the calibration characteristics is included. In preferred embodiments, the reference source is a blood glucose meter, and the at least two reference glucose values are obtained from blood tests. In additional embodiments, calculation of the calibration characteristics includes linear regression and, in particular embodiments, least squares linear regression. Alternatively, calculation of the calibration characteristics includes non-linear regression. Data integrity may be verified and the data may be filtered.

20 Claims, 18 Drawing Sheets
(1 of 18 Drawing Sheet(s) Filed in Color)

(51) Int. Cl.

| | |
|---|---|
| *G06G 7/48* | (2006.01) |
| *G06G 7/58* | (2006.01) |
| *A61B 5/00* | (2006.01) |
| *A61B 5/145* | (2006.01) |
| *A61B 5/1486* | (2006.01) |
| *A61B 5/1495* | (2006.01) |
| *A61M 5/172* | (2006.01) |

(52) U.S. Cl.
CPC ......... *A61B5/14546* (2013.01); *A61B 5/14865* (2013.01); *A61B 5/6848* (2013.01); *A61B 5/0002* (2013.01); *A61B 2560/0223* (2013.01); *A61M 2005/1726* (2013.01)

(56) References Cited

U.S. PATENT DOCUMENTS

| | | | |
|---|---|---|---|
| 4,678,408 | A | 7/1987 | Nason et al. |
| 4,685,903 | A | 8/1987 | Cable et al. |
| 4,786,394 | A | 11/1988 | Enzer et al. |
| 5,068,536 | A | 11/1991 | Rosenthal |
| 5,108,819 | A | 4/1992 | Heller et al. |
| 5,299,571 | A | 4/1994 | Mastrototaro |
| 5,390,671 | A | 2/1995 | Lord et al. |
| 5,391,250 | A | 2/1995 | Cheney, II et al. |
| 5,482,473 | A | 1/1996 | Lord et al. |
| 5,497,772 | A | 3/1996 | Schulman et al. |
| 5,507,288 | A | 4/1996 | Bocker et al. |
| 5,586,553 | A | 12/1996 | Halili et al. |
| 5,771,890 | A | 6/1998 | Tamada |
| 5,777,060 | A | 7/1998 | Van Antwerp |
| 5,786,439 | A | 7/1998 | Van Antwerp et al. |
| 5,796,606 | A * | 8/1998 | Spring ............... 700/9 |
| 5,813,403 | A | 9/1998 | Soller et al. |
| 5,830,133 | A | 11/1998 | Osten et al. |
| 5,875,109 | A * | 2/1999 | Federspiel ............... 700/40 |
| 5,885,211 | A | 3/1999 | Eppstein et al. |
| 5,965,380 | A | 10/1999 | Heller et al. |
| 6,001,065 | A | 12/1999 | DeVito |
| 6,049,727 | A | 4/2000 | Crothall |
| 6,069,011 | A | 5/2000 | Riedel |
| 6,088,608 | A | 7/2000 | Schulman et al. |
| 6,180,416 | B1 | 1/2001 | Kurnik et al. |
| 6,233,471 | B1 | 5/2001 | Berner et al. |
| 6,326,160 | B1 | 12/2001 | Dunn et al. |
| 6,424,847 | B1 | 7/2002 | Mastrototaro et al. |
| 6,424,873 | B1 | 7/2002 | Przybylski |
| 6,453,279 | B1 | 9/2002 | Prasad et al. |
| 6,895,263 | B2 | 5/2005 | Shin et al. |
| 7,267,665 | B2 | 9/2007 | Steil et al. |
| 2002/0161288 | A1 | 10/2002 | Shin et al. |
| 2003/0100040 | A1 | 5/2003 | Bonnecaze et al. |
| 2003/0235817 | A1 | 12/2003 | Bartkowiak |
| 2005/0043598 | A1 | 2/2005 | Goode, Jr. et al. |
| 2005/0143635 | A1 | 6/2005 | Kamath et al. |

FOREIGN PATENT DOCUMENTS

| | | |
|---|---|---|
| WO | WO 98/56293 | 12/1998 |
| WO | WO-99/29230 | 6/1999 |
| WO | WO 99/45375 | 9/1999 |
| WO | WO 99/45387 | 9/1999 |
| WO | WO 99/56613 | 11/1999 |
| WO | WO-99/58050 | 11/1999 |
| WO | WO-00/49941 | 8/2000 |

OTHER PUBLICATIONS

Partial PCT International Search Report issued in Application Number: PCT/US2004/044086, Mailing date May 17, 2005.
Office Action dated Feb. 13, 2009 from related EP patent application No. 04816061.8.
Search Report dated Oct. 24, 2005 from related PCT application No. PCT/US2004/044086.
US Office Action on DTD Jun. 11, 2010.
Office Action dated Aug. 17, 2010 from related Japanese patent application No. 2006-547604.
Office Action dated Oct. 2, 2007 from related EP patent application No. 04816061.8.
Notice of Allowance for U.S. Appl. No. 09/511,580 dated Mar. 14, 2002.
Notice of Allowance for U.S. Appl. No. 10/750,978 dated Jan. 28, 2010.
Notice of Allowance U.S. Appl. No. 10/141,375 dated May 17, 2004.
Office Action for U.S. Appl. No. 10/141,375 dated Jan. 8, 2004.
Office Action for U.S. Appl. No. 10/141,375 dated Jun. 24, 2003.
Office Action for U.S. Appl. No. 10/750,978 dated Jul. 2, 2009.
Office Action for U.S. Appl. No. 10/750,978 dated Nov. 14, 2008.
Office Action U.S. Appl. No. 09/511,580 dated Jul. 31, 2001.
Requirement for Restriction for U.S. Appl. No. 10/750,978 dated Jun. 27, 2008.
Supplemental Notice of Allowance for U.S. Appl. No. 10/141,375 dated Mar. 2, 2005.
Csöregi. E., et al., "Design, Characterization, and One-Point in Vivo Calibration of a Subcutaneously Implanted Glucose Electrode," Anal. Chem. 66:3131-3138 (1994).
Poitout, V., et al.. "Calibration in dogs of a subcutaneous miniaturized glucose sensor using a glucose meter for blood glucose determination," Biosensors & Bioelectronics 7:587-592 (1992).
Schmidtke, D.W., et al.. "Accuracy of the One-Point in Vivo Calibration of "Wired" Glucose Oxidase Electrodes Implanted in Jugular Veins of Rats in Periods of Rapid Rise and Decline of the Glucose Concentration," Anal. Chem. 70:2149-2155 (1998).
Velho. G., et al.. "Strategies for calibrating a subcutaneous glucose sensor," Biomed. Biochim. 48(11-12):957-964 (1989).
Von Woedtke, et al. "In situ calibration of implanted electrochemical glucose sensors." Biomed. Biochim. Acta. 48(11-12). 943-952 (1989).
Notice of Allowance dated Dec. 16, 2010 from related U.S. Appl. No. 10/750,978.
Office Action dated Jan. 31, 2011 from related European Patent Application No. 04816061.8.
Office Action dated Jul. 2, 2009 from related U.S. Appl. No. 10/750,978.

* cited by examiner

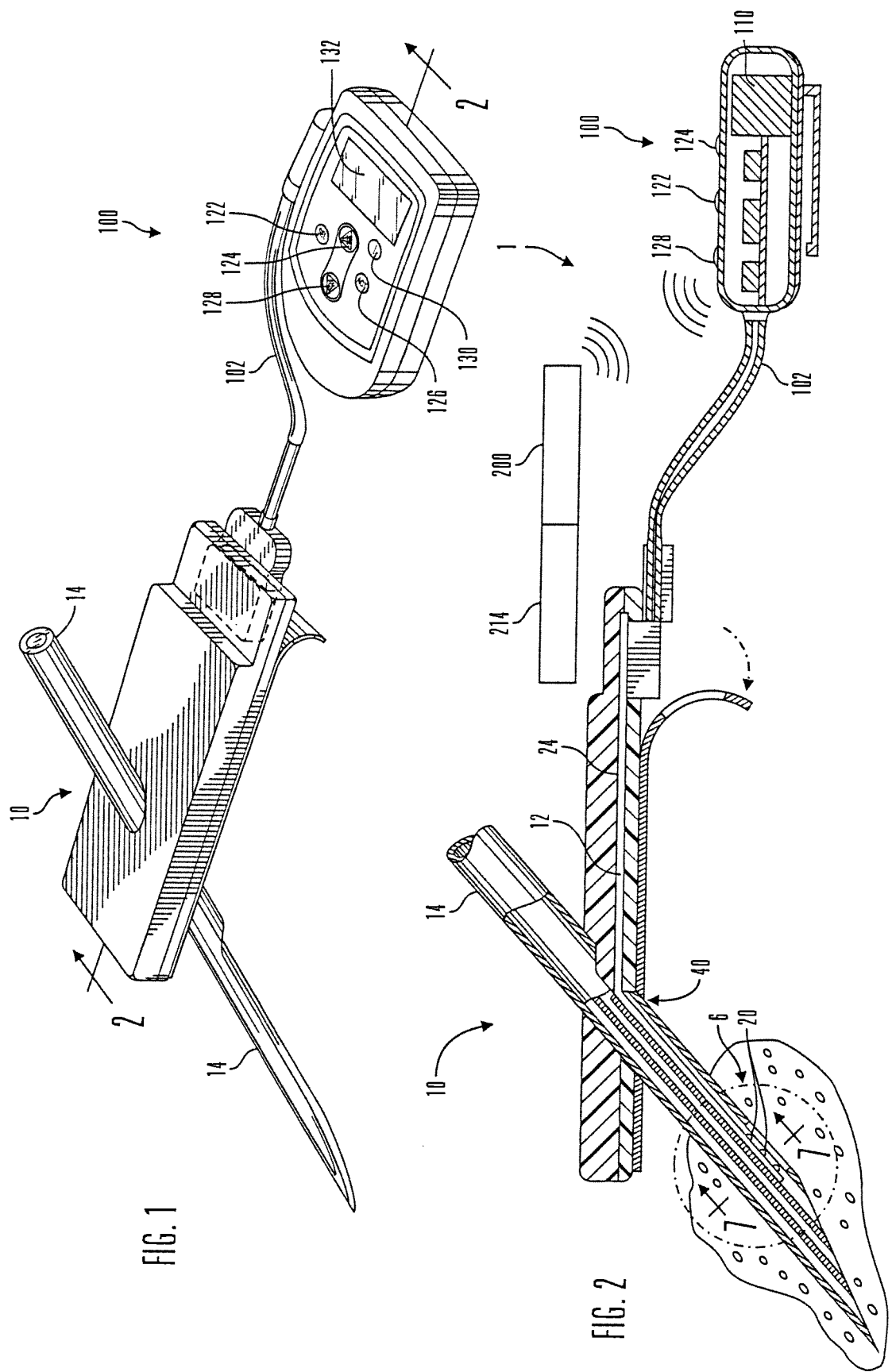

FIG. 10

| | A | B | C | D | E | F | G | H | I | J | K | L | M | N | O | P |
|---|---|---|---|---|---|---|---|---|---|---|---|---|---|---|---|---|
| 1 | PATIENT ID | SAMPLE | DATE | TIME | ISIG VALUE | VCTR | METER VALUE | SLOPE | OFFSET | VALID ISIG | SENSOR VALUE | SENSOR POWER UP | POWER DOWN | SENSOR INITIALIZATION | LINK EVENT | SENSOR DISCONNECT |
| 2 | 000-0000 | 0 | 7/10/98 | 10:53 | 0 | -2.042 | | | | | | | | | | |
| 3 | 000-0000 | 1 | 7/10/98 | 10:58 | 0 | -2.026 | | | | | | | | | | SEDI |
| 4 | 000-0000 | 2 | 7/10/98 | 11:03 | 0 | -1.732 | | | | | | | | | | |
| 5 | 000-0000 | 3 | 7/10/98 | 11:09 | 99.1 | -0.936 | | | | | | | | | | |
| 6 | 000-0000 | 4 | 7/10/98 | 11:14 | 19.7 | -0.565 | | | | | | | | | | |
| 7 | 000-0000 | 5 | 7/10/98 | 11:19 | 26.1 | -0.598 | | | | | | | | | | |
| 8 | 000-0000 | 6 | 7/10/98 | 11:24 | 25.7 | -0.626 | | | | | | | | | | |
| 9 | 000-0000 | 7 | 7/10/98 | 11:29 | 26 | -0.643 | | | | | | | | | | |
| 10 | 000-0000 | 8 | 7/10/98 | 11:34 | 24.9 | -0.648 | | | | | | | | | | |
| 11 | 000-0000 | 9 | 7/10/98 | 11:39 | 23.9 | -0.649 | | | | | | | | | | |
| 12 | 000-0000 | 10 | 7/10/98 | 11:44 | 23.8 | -0.651 | | | | | | | | | | |
| 13 | 000-0000 | 11 | 7/10/98 | 11:49 | 24.3 | -0.658 | | | | | | | | | | |
| 14 | 000-0000 | 12 | 7/10/98 | 11:54 | 23.9 | -0.655 | | | | | | | | | | |
| 15 | 000-0000 | 13 | 7/10/98 | 11:59 | 23 | -0.652 | | | | | | | | | | |
| 16 | 000-0000 | 14 | 7/10/98 | 12:04 | 23.3 | -0.652 | | | | | | | | | | |
| 17 | 000-0000 | 15 | 7/10/98 | 12:09 | 22.2 | -0.645 | | | | | | | | | | |
| 18 | 000-0000 | 16 | 7/10/98 | 12:14 | 22.1 | -0.644 | 95 | 5.0 | 3 | 22.1 | 96 | | | | | |
| 19 | 000-0000 | 17 | 7/10/98 | 12:19 | 20.1 | -0.634 | | | | 20.1 | 86 | | | | | |
| 20 | 000-0000 | 18 | 7/10/98 | 12:24 | 19.9 | -0.637 | | | | 19.9 | 85 | | | | | |
| 21 | 000-0000 | 19 | 7/10/98 | 12:29 | 20.6 | -0.645 | | | | 20.6 | 88 | | | | | |
| 22 | 000-0000 | 20 | 7/10/98 | 12:34 | 20.8 | -0.662 | | | | 20.8 | 89 | | | | | |
| 23 | 000-0000 | 21 | 7/10/98 | 12:39 | 19.1 | -0.645 | | | | 19.1 | 81 | | | ESI | | |
| 24 | 000-0000 | 22 | 7/10/98 | 12:44 | 18.2 | -0.635 | | | | 18.2 | 76 | | | | | |
| 25 | 000-0000 | 23 | 7/10/98 | 12:49 | 17.4 | -0.633 | | | | 17.4 | 72 | | | | | |
| 26 | 000-0000 | 24 | 7/10/98 | 12:54 | 16.4 | -0.625 | | | | 16.4 | 67 | | | | | |
| 27 | 000-0000 | 25 | 7/10/98 | 12:59 | 15.7 | -0.619 | | | | 15.7 | 64 | | | | | |
| 28 | 000-0000 | 26 | 7/10/98 | 13:04 | 15 | -0.612 | | | | 15 | 60 | | | | | |
| 29 | 000-0000 | 27 | 7/10/98 | 13:09 | 13.8 | -0.602 | | | | 13.8 | 54 | | | | | |
| 30 | 000-0000 | 28 | 7/10/98 | 13:14 | 13.3 | -0.597 | | | | 13.3 | 52 | | | | | |
| 31 | 000-0000 | 29 | 7/10/98 | 13:19 | 14.4 | -0.62 | | | | 14.4 | 57 | | | | | |
| 32 | 000-0000 | 30 | 7/10/98 | 13:24 | 16 | -0.635 | | | | 16 | 65 | | | | | |

Noisy sensor signal 2200

High amplitude second-order derivative 2210

REAL TIME SELF-ADJUSTING CALIBRATION ALGORITHM

CROSS-REFERENCE TO RELATED APPLICATIONS

This application is a continuation-in-part of U.S. patent application Ser. No. 10/141,375, filed May 8, 2002, and entitled "Real Time Self-Adjusting Calibration Algorithm," which itself is a continuation-in-part of U.S. patent application Ser. No. 09/511,580, filed Feb. 23, 2000, and entitled "Glucose Monitor Calibration Methods", now U.S. Pat. No. 6,424,847, both of which are herein incorporated by reference in their entirety and from which priority is claimed.

FIELD OF THE INVENTION

This invention relates to glucose monitor systems and, in particular embodiments, to calibration methods for glucose monitoring systems.

BACKGROUND OF THE INVENTION

Over the years, body characteristics have been determined by obtaining a sample of bodily fluid. For example, diabetics often test for blood glucose levels. Traditional blood glucose determinations have utilized a painful finger prick using a lancet to withdraw a small blood sample. This results in discomfort from the lancet as it contacts nerves in the subcutaneous tissue. The pain of lancing and the cumulative discomfort from multiple needle pricks is a strong reason why patients fail to comply with a medical testing regimen used to determine a change in a body characteristic over a period of time. Although non-invasive systems have been proposed, or are in development, none to date have been commercialized that are effective and provide accurate results. In addition, all of these systems are designed to provide data at discrete points and do not provide continuous data to show the variations in the characteristic between testing times.

A variety of implantable electrochemical sensors have been developed for detecting and/or quantifying specific agents or compositions in a patient's blood. For instance, glucose sensors are being developed for use in obtaining an indication of blood glucose levels in a diabetic patient. Such readings are useful in monitoring and/or adjusting a treatment regimen which typically includes the regular administration of insulin to the patient. Thus, blood glucose readings improve medical therapies with semi-automated medication infusion pumps of the external type, as generally described in U.S. Pat. Nos. 4,562,751; 4,678,408; and 4,685,903; or automated implantable medication infusion pumps, as generally described in U.S. Pat. No. 4,573,994, which are herein incorporated by reference. Typical thin film sensors are described in commonly assigned U.S. Pat. Nos. 5,390,671; 5,391,250; 5,482,473; and 5,586,553 which are incorporated by reference herein. See also U.S. Pat. No. 5,299,571.

SUMMARY OF THE DISCLOSURE

It is an object of an embodiment of the present invention to provide an improved glucose monitor system and method, which obviates for practical purposes, the above mentioned limitations.

According to an embodiment of the invention, a method of calibrating glucose monitor data includes obtaining glucose monitor data at predetermined intervals over a period of time. It also includes obtaining at least two reference glucose values from a reference source that correspond with the glucose monitor data obtained at the predetermined intervals. Additionally, calculating calibration characteristics using the at least two reference values and the corresponding glucose monitor data to regress the obtained glucose monitor data is included. And calibrating the obtained glucose monitor data using the calibration characteristics is included. In preferred embodiments, the reference source is a blood glucose meter, and the at least two reference glucose values are obtained from blood tests. In additional embodiments, the calculation of the calibration characteristics is obtained using linear regression, and in particular embodiments, using least squares linear regression. Alternatively, the calculation of the calibration characteristics is obtained using non-linear regression or a non-regression technique.

In particular embodiments, the predetermined period of time is a 24 hour period, and the predetermined intervals are 5 minute intervals. Further embodiments may include the step of shifting the data by a predetermined time factor, such as for example, ten minutes. Preferably, the calibration is performed while obtaining glucose monitor data. However, alternative embodiments may perform the calibration on glucose monitor data that has been collected for post processing by another processing device.

According to an embodiment of the invention, a method of calibrating glucose monitor data includes obtaining glucose monitor data at a predetermined memory storage rate. Also included is obtaining at least one blood glucose reference reading from a blood glucose measuring device that corresponds with at least one glucose monitor data point obtained at the predetermined memory storage rate. Calculating a calibration factor using the at least one blood glucose reference reading and the corresponding at least one glucose monitor data point is included. And calibrating the obtained glucose monitor data using the calibration factor is included. In preferred embodiments, after a first calibration factor is calculated, at least one previous calibration factor is used with at least one blood glucose reference reading from a blood glucose measuring device and its at least one corresponding glucose monitor data point to calculate a calibration factor. In additional embodiments, at least two blood glucose reference readings are used for calibration. In further embodiments, the calculation of the calibration factor is obtained using linear regression, and in particular least squares linear regression. Alternatively, calculation of the calibration factor uses non-linear regression or a non-regression technique In particular embodiments, the calibration factor is applied to glucose monitor data obtained before a last blood glucose reference reading from a blood glucose measuring device that corresponds with at least one glucose monitor data point obtained at a predetermined memory storage rate is used to calculate the calibration factor. Alternatively, the calibration factor is applied to glucose monitor data obtained after the last blood glucose reference reading from a blood glucose measuring device that is used to calculate the calibration factor.

In particular embodiments, the predetermined memory storage rate is once every 5 minutes. And the glucose monitor data that is obtained at a predetermined memory storage rate is the result of utilizing at least 2 sample values sampled from a glucose sensor at a rate faster than the memory storage rate.

In preferred embodiments, at least one blood glucose reference reading from a blood glucose measuring device is obtained during a predetermined calibration period, and a calibration factor is calculated using those readings after every predetermined calibration period. In particular embodiments, the predetermined calibration period is 24 hours. In further preferred embodiments, a predetermined time shift is used to temporally correlate the at least one blood glucose reference reading from a blood glucose measuring device with the at least one glucose monitor data point obtained at the predetermined memory storage rate. In particular embodiments, the predetermined time shift is ten minutes.

In particular embodiments, one or more calculations for calculating a first calibration factor is different from the one or more calculations for calculating subsequent calibration factors. In other particular embodiments, the calculation for calculating a first calibration factor uses a single-point calibration equation. In further particular embodiments, the single-point calibration equation includes an offset value. In other particular embodiments, the one or more calculations for calculating a calibration factor other than the first calibration factor uses a linear regression calibration equation, a non-linear regression calibration equation, or a non-regression technique.

According to an embodiment of the invention, a method of calibrating glucose monitor data includes obtaining glucose monitor data. It also includes obtaining from another blood glucose measuring device at least one blood glucose reference reading that is temporally associated with at least one glucose monitor data reading. Determining a calibration equation using the at least one blood glucose reference reading and the corresponding at least one glucose monitor data reading is also included. And calibrating the glucose monitor data using the calibration equation is included.

According to another embodiment of the invention, a method of calibrating body characteristic monitor data includes obtaining body characteristic monitor data. It also includes obtaining from another characteristic measuring device at least one characteristic reference reading that is temporally associated with at least one characteristic monitor data point. Calculating calibration characteristics using the at least one characteristic reference reading and the corresponding at least one characteristic monitor data point is included. And calibrating the obtained characteristic monitor data using the calibration characteristics is included. In particular embodiments, at least two body characteristic reference readings are used for calculating the calibration characteristics. In particular embodiments, the calculation for calculating the calibration characteristics is a linear regression calculation.

According to additional embodiments of the invention, an apparatus for calibrating glucose monitor data includes a glucose monitor, glucose sensor, a blood glucose meter and a processor. The glucose monitor includes a glucose monitor memory for storing glucose monitor data. The glucose sensor is electronically coupled to the glucose monitor to supply the glucose monitor data. The blood glucose measuring device provides at least one blood glucose reference reading that is temporally associated with at least one glucose monitor data point. And the processor includes software to calculate calibration characteristics using the at least one blood glucose reference reading that is temporally associated with at least one glucose monitor data point, and the processor applies the calibration characteristics to the glucose monitor data. In particular embodiments, the at least one blood glucose reading is entered into the glucose monitor. In particular embodiments, the glucose monitor includes the processor, or alternatively, the processor is in a separate device that receives glucose monitor data from the glucose monitor.

In other embodiments of the invention, an apparatus for calibrating glucose monitor data includes means for obtaining glucose monitor data. It also includes means for obtaining from another blood glucose measuring device at least one blood glucose reference reading that is temporally associated with at least one glucose monitor data reading. Means for calculating a calibration equation using the at least one blood glucose reference reading and the corresponding at least one glucose monitor data reading is included. And means for calibrating the glucose monitor data using the calibration equation is also included.

According to an embodiment of the present invention, a method for verifying the integrity of sensor data may include receiving a first data value from the sensor; comparing a first parameter relating to the first data value to a first threshold value; receiving a second data value from the sensor; comparing a first parameter relating to the second data value to the first threshold value; continuing receipt of data from the sensor when the first parameter relating to the first data value exceeds the first threshold value and the first parameter relating to the second data value does not exceed the first threshold value; and terminating receipt of data from the sensor when the first parameter relating to the first data value and the first parameter relating to the second data value exceed the first threshold value. The sensor may be a glucose sensor. The data value may be a blood glucose concentration.

The method may also include discarding the first data value when the first parameter relating to the first data value exceeds the first threshold value and the first parameter relating to the second data value does not exceed the first threshold value. The first parameter relating to the first data value may be a second-order derivative of the first data value and the first parameter relating to the second data value may be a second-order derivative of the second data value. The first parameter relating to the first data value may also be a first-order derivative of the first data value the first parameter relating to the second data value may also be a first-order derivative of the second data value.

The method may further include comparing a second parameter relating to the first data value to a second threshold value; continuing receipt of data from the sensor when the first parameter relating to the first data value exceeds the first threshold value, the second parameter relating to the first data value exceeds the second threshold value, and the first parameter relating to the second data value does not exceed the first threshold value; terminating receipt of data from the sensor when the first parameter relating to the first data value exceeds the first threshold value, the second parameter relating to the first data value exceeds the second threshold value, and the first parameter relating to the second data value exceeds the first threshold value.

The method may further include discarding the first data value when the first parameter relating to the first data value exceeds the first threshold value, the second parameter relating to the first data value exceeds the second threshold value, and the first parameter relating to the second data value does not exceed the first threshold value. The first parameter relating to the first data value may be a second-order derivative of the first data value, the first parameter relating to the second data value may be a second-order derivative of the second data value, and the second parameter relating to the first data value may be a first-order derivative.

Terminating receipt of data from the sensor may occur when first parameter relating to the second data value exceeds the first threshold value within a predetermined period of time. Terminating receipt of data from the sensor may also occur when the first parameter relating to the second data value exceeds the first threshold value within a predetermined period of time. The first and second thresholds may vary depending on the blood glucose concentration.

According to an embodiment of the present invention, a method for filtering data from a sensor may include receiving a plurality of data values from the sensor; obtaining a quantifier of a variance of a measurement error associated with the plurality of data values; and filtering the plurality of data values with an adaptive filter. The quantifier may be an input to the adaptive filter. The sensor may be a glucose sensor. The plurality of data values may be blood glucose concentrations.

Obtaining a quantifier may include formulating a standard deviation of an absolute value of consecutive data points within the plurality of data points. Formulating the standard deviation may include formulating a windowed, unweighted standard deviation or a recursive, weighted standard deviation. The adaptive filter may be a Kalman filter.

According to an embodiment of the present invention, a method for calibrating a sensor may include receiving a plurality of data values from the sensor; determining the reliability of each data value of the plurality of data values; discarding data values of the plurality of data values that are unreliable; filtering the data values of the plurality of data that have not been discarded; and adjusting an output of the sensor using the filtered data values. The sensor may be a glucose sensor and the plurality of data values may be blood glucose concentrations.

Determining the reliability of each data value may include comparing each data value to a predetermined threshold or comparing a parameter related to each data value to a predetermined threshold. The parameter may be a second-order derivative or a first-order derivative. The predetermined threshold may vary depending on a current plurality of data values. The current plurality of data values may be blood glucose concentrations.

Discarding data values may include discarding data values that do not meet a pre-established criterion related to the predetermined threshold. Filtering the data values may include filtering the data values with an adaptive filter. The adaptive filter may be a Kalman filter.

Filtering the data values with an adaptive filter may include using the adaptive filter with a parameter based on the data values of the plurality of data that have not been discarded. The parameter may be a standard deviation of the data values of the plurality of data that have not been discarded. Also, the parameter may be a standard deviation of an absolute value of data values within the data values of the plurality of data that have not been discarded. The standard deviation may be a windowed, unweighted standard deviation or may be a recursive, weighted standard deviation.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

A detailed description of embodiments of the invention will be made with reference to the accompanying drawings, wherein like numerals designate corresponding parts in the several figures.

FIG. 1 is a is a perspective view illustrating a subcutaneous glucose sensor insertion set and glucose monitor device in accordance with an embodiment of the present invention;

FIG. 2 is a cross-sectional view of the sensor set and glucose monitor device as shown along the line 2-2 of FIG. 1;

FIG. 10 is a sample computer screen image of a post processor analysis of glucose monitor data;

DETAILED DESCRIPTION OF THE PREFERRED EMBODIMENTS

Figure 3:
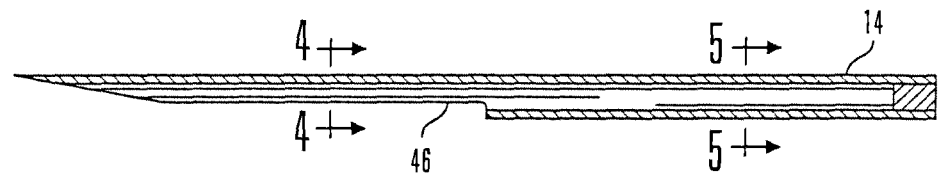
FIG. 3 is a cross-sectional view of a slotted insertion needle used in the insertion set of FIGS. 1 and 2.
Figure 4:
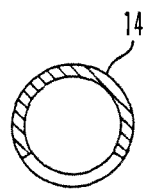
FIG. 4 is a cross-sectional view as shown along line 4-4 of FIG. 3.
Figure 5:
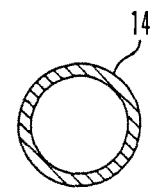
FIG. 5 is a cross-sectional view as shown along line 5-5 of FIG. 3.
Figure 6:
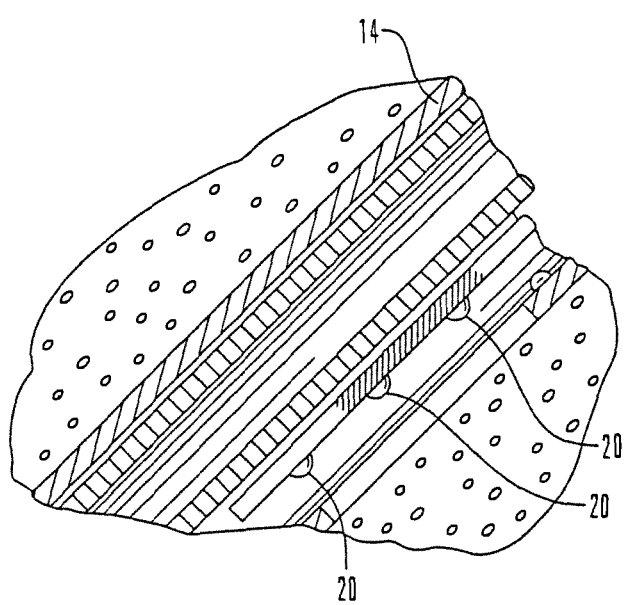
FIG. 6 is a partial cross-sectional view corresponding generally with the encircled region 6 of FIG. 2.
Figure 7:
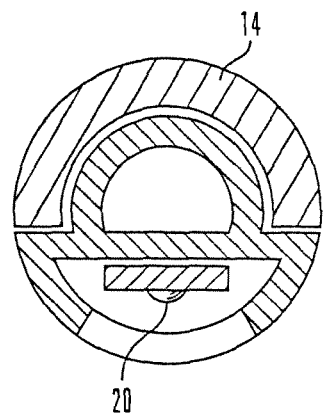
FIG. 7 is a cross-sectional view as shown along line 7-7 of FIG. 2.

As shown in the drawings for purposes of illustration, the invention is embodied in calibration methods for a glucose monitor that is coupled to a sensor set to provide continuous data recording of readings of glucose levels from a sensor for a period of time. In preferred embodiments of the present invention, the sensor and monitor are a glucose sensor and a glucose monitor for determining glucose levels in the blood and/or bodily fluids of a user. However, it will be recognized that further embodiments of the invention may be used to determine the levels of other body characteristics including analytes or agents, compounds or compositions, such as hormones, cholesterol, medications concentrations, viral loads (e.g., HIV), bacterial levels, or the like. The glucose sensor is primarily adapted for use in subcutaneous human tissue.

However, in still further embodiments, one or more sensors may be placed in other tissue types, such as muscle, lymph, organ tissue, veins, arteries or the like, and used in animal tissue to measure body characteristics. Embodiments may record readings from the sensor on an intermittent, periodic, on-demand, continuous, or analog basis.

FIGS. 1-7 illustrate a glucose monitor system 1 for use with the calibration methods. The glucose monitor system 1, in accordance with a preferred embodiments of the present invention, includes a subcutaneous glucose sensor set 10 and a glucose monitor 100. In preferred embodiments, the glucose monitor 100 is of the type described in U.S. Patent Application Ser. No. 60/121,664, filed on Feb. 25, 1999, entitled "Glucose Monitor System", which is herein incorporated by reference. In alternative embodiments, the glucose monitor is of the type described in U.S. patent application Ser. No. 09/377,472, filed Aug. 19, 1999, entitled "Telemetered Characteristic Monitor System And Method Of Using The Same", which is incorporated by reference herein.

Preferably, the glucose monitor 100 is worn by the user and is connected to a surface mounted glucose sensor set 10 that is attached to a user's body by an electrically conductive cable 102, of the type described in U.S. Patent Application Ser. No. 60/121,656, filed on Feb. 25, 1999, entitled "Test Plug and Cable for a Glucose Monitor", which is incorporated by reference herein. In preferred embodiments, the sensor interface may be configured in the form of a jack to accept different types of cables that provide adaptability of the glucose monitor 100 to work with different types of subcutaneous glucose sensors and/or glucose sensors placed in different locations of the user's body. However, in alternative embodiments, the sensor interface is permanently connected to the cable 102. In additional alternative embodiments, a characteristic monitor is connected to one or more sensor sets to record data of one or more body characteristics from one or more locations on or in the user's body.

The glucose sensor set 10 is of the type described in U.S. Patent Application Ser. No. 60/121,655, filed on Feb. 25, 1999, entitled "Glucose Sensor Set", or U.S. patent Ser. No. 08/871,831, filed on Jun. 9, 1997, entitled "Insertion Set For A Transcutaneous Sensor", which are incorporated by reference herein. The glucose sensor 12, of the type described in U.S. patent application Ser. No. 29/101,218, filed on Feb. 25, 1999, entitled "Glucose Sensor", or described in commonly assigned U.S. Pat. Nos. 5,390,671; 5,391,250; 5,482,473; and 5,586,553 which are incorporated by reference herein; extends from the glucose sensor set 10 into the user's body with electrodes 20 of the glucose sensor 12 terminating in the user's subcutaneous tissue. See also U.S. Pat. No. 5,299,571. However, in alternative embodiments, the glucose sensor 12 may use other types of sensors, such as chemical based, optical based, or the like. In further alternative embodiments, the sensors may be of a type that is used on the external surface of the skin or placed below the skin layer of the user for detecting body characteristics.

The glucose monitor 100 generally includes the capability to record and store data as it is received from the glucose sensor 12, and includes either a data port (not shown) or wireless transmitter and/or receiver (also not shown) for transferring data to and/or from a data processor 200 such as a computer, communication station, a dedicated processor designed specifically to work with the glucose monitor, or the like. The glucose monitor is generally of the type described in U.S. patent application Ser. No. 09/377,472, filed Aug. 19, 1999, entitled "Telemetered Characteristic Monitor System And Method Of Using The Same", which is incorporated by reference herein.

Preferably, the glucose monitor system 1 minimizes inconvenience by separating complicated monitoring process electronics into two separate devices; the glucose monitor 100, which attaches to the glucose sensor set 10; and the data processor 200, which contains the software and programming instructions to download and evaluate data recorded by the glucose monitor 100. In addition, the use of multiple components (e.g., glucose monitor 100 and data processor 200) facilitates upgrades or replacements, since one module, or the other, can be modified, re-programmed, or replaced without requiring complete replacement of the monitor system 1. Further, the use of multiple components can improve the economics of manufacturing, since some components may require replacement on a more frequent basis, sizing requirements may be different for each module, different assembly environment requirements, and modifications can be made without affecting the other components.

The glucose monitor 100 takes raw glucose sensor data from the glucose sensor 12 and assesses it during real-time and/or stores it for later processing or downloading to the data processor 200, which in turn analyzes, displays, and logs the received data. The data processor 200 utilizes the recorded data from the glucose monitor 100 to analyze and review the blood glucose history. In particular embodiments, the glucose monitor 100 is placed into a com-station which facilitates downloading data to a personal computer for presentation to a physician. A software is used to download the data, create a data file, calibrate the data, and display the data in various formats including charts, forms, reports, graphs, tables, lists, and the like. In further embodiments, the glucose monitor system 1 may be used in a hospital environment or the like.

In alternative embodiments, the glucose monitor includes at least portions of the software described as contained within the data processor 200 above. The glucose monitor might contain the necessary software to calibrate glucose sensor signals, display a real-time blood glucose value, show blood glucose trends, activate alarms and the like. A glucose monitor with these added capabilities is useful for patients that might benefit from real-time observations of their blood glucose characteristics even while they're not in close proximity to a computer, communication device or dedicated independent data processor.

As shown in FIG. 2, the data processor 200, may include a display 214 that is used to display the calculated results of the raw glucose sensor data received via a download from the glucose monitor 100. The results and information displayed includes, but is not limited to, trending information of the characteristic (e.g., rate of change of glucose), graphs of historical data, average characteristic levels (e.g., glucose), stabilization and calibration information, raw data, tables (showing raw data correlated with the date, time, sample number, corresponding blood glucose level, alarm messages, and more), and the like. Alternative embodiments include the ability to scroll through the data. The display 214 may also be used with buttons (not shown) on the data processor 200, computer, communication station, characteristic monitor, or the like, to program or update data. In preferred embodiments, the glucose monitor 100 includes a display 132 to assist the user in programming the glucose monitor 100, entering data, stabilizing, calibrating, downloading data, or the like.

Still further embodiments of the present invention may include one or more buttons 122, 124, 126 and 128 on the glucose monitor 100 to program the monitor 100, to record data, insert flags to correlate data with external events for later analysis, input calibration values, or the like. In addition, the glucose monitor 100 may include an on/off button 130 for compliance with safety standards and regulations to temporarily suspend transmissions or recording. The glucose monitor 100 may also be combined with other medical devices to accept other patient data through a common data network and/or telemetry system. The glucose monitor 100 may be combined with a blood glucose meter to directly import or correlate glucose calibration reference values such as described in U.S. patent application Ser. No. 09/334,996, filed Jun. 17, 1999, entitled "Characteristic Monitor With A Characteristic Meter and Method Of Using The Same", which is incorporated by reference herein. The glucose monitor 100 may also be combined with semi-automated medication infusion pumps of the external type, as generally described in U.S. Pat. Nos. 4,562,751; 4,678,408; and 4,685,903; or automated implantable medication infusion pumps, as generally described in U.S. Pat. No. 4,573,994, which are herein incorporated by reference. The glucose monitor 100 may record data from the infusion pumps and/or may process data from both the glucose sensor 12 and an infusion pump to establish a closed loop system to control the infusion pump based on glucose sensor measurements. In other embodiments, other body characteristics are monitored, and the monitor may be used to provide feedback in a closed loop system to control a drug delivery rate. In further alternative embodiments, the glucose monitor 100 can be combined with a glucose sensor set 10 as a single unit.

Glucose sensors are replaced periodically to avoid infection, decaying enzyme coating and therefore sensor sensitivity, deoxidization of the electrodes, and the like. The user will disconnect the glucose sensor set 10 from the cable 102 and glucose monitor 100. A needle 14 is used to install another glucose sensor set 10 and then the needle 14 is removed. Further description of the needle 14 and the sensor set 10 are found in U.S. Pat. No. 5,586,553, entitled "Transcutaneous Sensor Insertion Set"; co-pending U.S. patent application Ser. No. 09/346,835, filed Jul. 2, 1999, entitled "Insertion Set For A Transcutaneous Sensor"; and U.S. Pat. No. 5,951,521, entitled "A Subcutaneous Implantable Sensor Set Having The Capability To Remove Or Deliver Fluids To An Insertion Site," which are herein incorporated by reference.

The user connects the connection portion 24 of the glucose sensor set 10 through the cable 102 to the glucose monitor 100, so that the glucose sensor 12 can then be used over a prolonged period of time. An initial reading may be downloaded from the glucose sensor set 10 and the glucose monitor 100 to the data processor 200, to verify proper operation of the glucose sensor 10 and the glucose monitor 100. In preferred embodiments, the glucose sensor set 10 provides data to the glucose monitor 100 for one to seven days before replacement. Glucose sensors 12 may last in the user's body for longer or shorter periods of time depending on the quality of the installation, cleanliness, the durability of the enzyme coating, deoxidization of the sensor, user's comfort, and the like.

After installation into the body, the glucose sensor 12 is initialized to achieve a steady state of operation before starting a calibration process. Preferably, power supplied by three series silver oxide 357 battery cells 110 in the glucose monitor 100 is used to speed the initialization of the glucose sensor 12. Alternatively, other power supplies may be used such as, different battery chemistries including lithium, alkaline, or the like, and different numbers of batteries, solar cells, a DC converter plugged into an AC socket (provided with proper electrical isolation), or the like.

The use of an initialization process can reduce the time for glucose sensor 12 stabilization from several hours to an hour or less. The preferred initialization procedure uses a two step process. First, a high voltage (preferably between 1.0-1.1 volts—although other voltages may be used) is applied between electrodes 20 of the sensor 12 for one to two minutes (although different time periods may be used) to allow the sensor 12 to stabilize. Then, a lower voltage (preferably between 0.5-0.6 volts—although other voltages may be used) is applied for the remainder of the initialization process (typically 58 minutes or less). Other stabilization/initialization procedures using differing currents, currents and voltages, different numbers of steps, or the like, may be used. Other embodiments may omit the initialization/stabilization process, if not required by the body characteristic sensor or if timing is not a factor. Alternatively, the characteristic monitor or the data processor 200 may apply an algorithm to the sensor data to determine when initial transients are sufficiently diminished and the sensor is at a significantly stable state to begin calibration.

In preferred embodiments, data is not considered valid until a sensor initialization event flag (ESI) is set in the data indicating that stabilization is complete. Preferably, stabilization is complete after 60 minutes or when a user enters a sensor initialization flag using one or more buttons on the glucose monitor 100. After stabilization/initialization is complete the glucose monitor 100 is calibrated to accurately interpret readings from the newly installed glucose sensor 12.

Beginning with the stabilization process, the glucose monitor 100 measures a continuous electrical current signal (ISIG) generated by the glucose sensor 12 relative to a concentration of glucose present in the subcutaneous tissue of the user's body. In preferred embodiments, the glucose monitor 100 samples the ISIG from the glucose sensor 12 at a sampling rate of once every 10 seconds, as shown in FIGS. 8*a*-*c*. Examples of sampled values are labeled A-AD in FIG. 8*a*. At an interval rate of once per minute, the highest and lowest of the sampled values (shown in FIG. 8*a* as circled sampled values A, E, G, I, M, R, V, W, Y, and AB) are ignored, and the remaining 4 sampled values from an interval are averaged to create interval values (shown in FIG. 8*b* as values F', L', R', X', and AD'). At a glucose monitor memory storage rate of once every 5 minutes, the highest and lowest of the interval values (shown in FIG. 8*b* as values L' and X') are ignored and the remaining 3 interval values are averaged and stored in a glucose monitor memory as memory values (shown in FIG. 8*c* as point AD"). The memory values are retained in memory and may be downloaded to the data processor 200. The memory values are used to calibrate the glucose monitor 100 and/or the post processor 200 and to analyze blood glucose levels. The sampling rate, interval rate and the memory storage rate may be varied as necessary to capture data with sufficient resolution to observe transients or other changes in the data depending on the rate at which sensor values can change, which is affected by the sensor sensitivity, the body characteristic being measured, the physical status of the user, and the like. In other embodiments, all of the sampled values are included in the average calculations of memory storage values. In alternative embodiments, more or less sampled values or interval values are ignored depending on the signal noise, sensor stability, or other causes of undesired transient readings. Finally, in still other embodiments, all sampled values and/or interval values are stored in memory.

Clipping limits may be used to limit the signal magnitude variation from one value to the next thereby reducing the effects of extraneous data, outlying data points, or transients. In preferred embodiments, clipping limits are applied to the interval values. For instance, interval values that are above a maximum clipping limit or below a minimum clipping limit are replaced with the nearest clipping limit value.

In alternative embodiments, interval values that are outside of the clipping limits are ignored and not used to calculate the next memory storage value. In particular embodiments, the detection of interval values outside of the clipping limits is considered a calibration cancellation event. In further particular embodiments, more than one value must be deemed outside of clipping limits to constitute a calibration cancellation event. (Calibration cancellation events are discussed below).

In preferred embodiments, the clipping limits are shifted after each data point. The level that the clipping limits are set to is dependent on an acceptable amount of change from the previous interval value to the present interval value, which is affected by the sensor sensitivity, signal noise, signal drift, and the like. In preferred embodiments, the clipping limits are calculated based on the magnitude of the previous interval value. For example, for a previous interval value from 0 up to but not including 15 Nano-Amps, the clipping limits are set at plus and minus 0.5 Nano-Amps about the previous interval value. For a previous interval value from 15 up to but not including 25 Nano-Amps, the clipping limits are set at plus and minus 3% of the previous interval value, about the previous interval value. For a previous interval value from 25 up to but not including 50 Nano-Amps, the clipping limits are set at plus and minus 2% of the previous interval value, about the previous interval value. And for a previous interval value of 50 Nano-Amps and greater, the clipping limits are set at plus and minus 1% about the previous interval value. In alternative embodiments, different clipping limits may be used.

Figure 9:
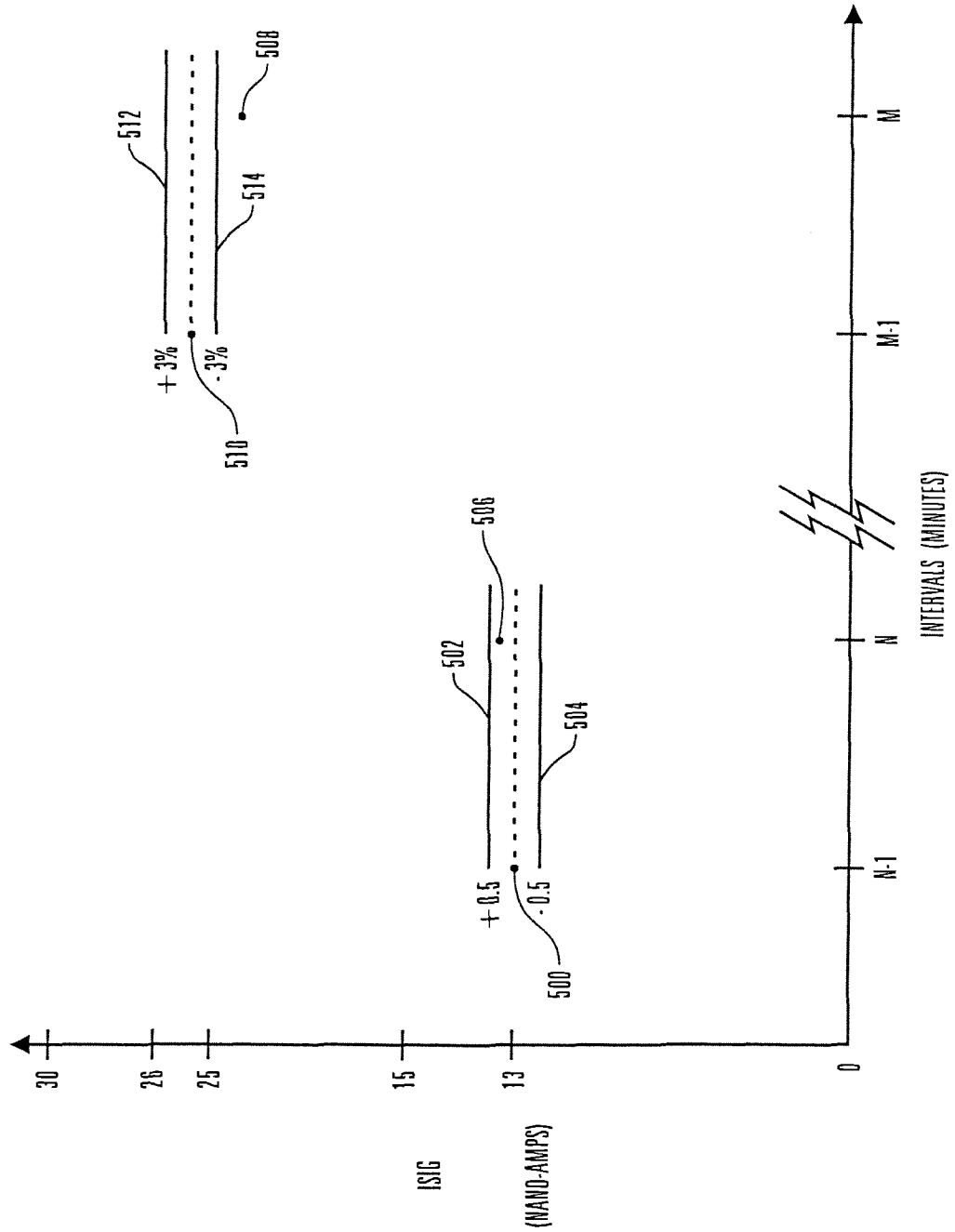
FIG. 9 is a chart showing clipping limits.

FIG. 9 shows a typical clipping limit example in which a previous interval value 500, associated with interval N−1, has a magnitude of 13.0 Nano-Amps, which is less than 15.0 Nano-Amps. Therefore, the maximum clipping limit 502 for the present interval value 506 is set at 13.5 Nano-Amps, which is 0.5 Nano-Amps greater than the magnitude of the previous interval value 500. And the minimum clipping limit 504 is set at 12.5 Nano-Amps which is 0.5 Nano-Amps below the previous interval value 500. The present interval value 506, associated with interval N, is between the maximum clipping limit 502 and the minimum clipping limit 504 and is therefore acceptable.

In another example shown in FIG. 9, the present interval value 508, associated with interval M, has a value of 25.0 Nano-Amps which is outside of the clipping limit 514 and will therefore be clipped. The previous interval value 510, associated with interval M−1, is 26.0 Nano-Amps, which is included in the range from 25.0 up to but not including 50.0 Nano-Amps as discussed above. Therefore the clipping limits are ±2%. The maximum clipping limit 512 is 2% greater than the previous interval value 510, 26.0+26.0*0.02=26.5 Nano-Amps.

Similarly the minimum clipping limit 514 is 2% less than the previous interval value 510, 26.0−26.0*0.02=25.5 Nano-Amps.

Figure 8:
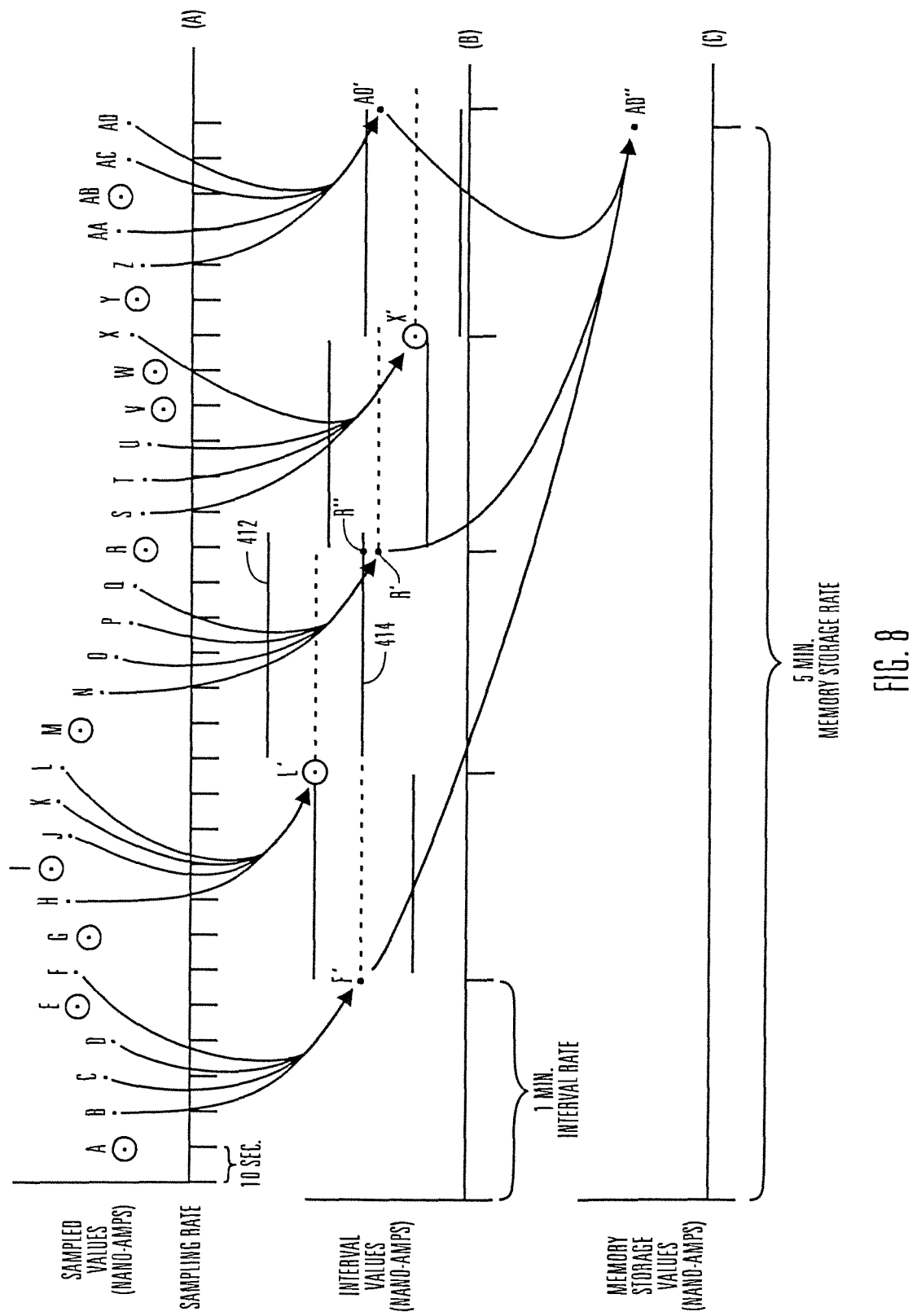
FIGS. 8(a-c) are diagrams showing a relationship between sampled values, interval values and memory storage values.

Since the present interval value 508 of 25.0 Nano-Amps is less than the minimum clipping limit 514 of 25.5 Nano-Amps, it will be clipped, and 25.5 Nano-Amps will be used in place of 25.0 Nano-Amps to calculate a memory storage value. For further illustration, FIG. 8 shows interval value R', which is calculated by averaging sampled values N through Q, is outside of the clipping limits 412 and 414, which result from the previous interval value L'. Therefore, the magnitude of interval value R' is not used to calculate memory value AD", instead R", which is the magnitude of the minimum clipping limit 414, is used.

In other embodiments, the clipping limits may be a smaller or larger number of Nano-Amps or a smaller or larger percentage of the previous interval value based on the sensor characteristics mentioned above. Alternatively, the clipping limits are calculated as plus or minus the same percent change from every previous interval value. Other algorithms use several interval values to extrapolate the next interval value and set the clipping limits to a percentage higher and lower than the next anticipated interval value. In further alternatives, clipping may be applied to the sampled values, interval values, memory values, calculated glucose values, estimated values of a measured characteristic, or any combination of the values.

In preferred embodiments, all interval values are compared to an out-of-range limit of 200 Nano-Amps. If three consecutive interval values are equal to or exceed the out-of-range limit, the sensor sensitivity is deemed to be too high and an alarm is activated to notify the user that re-calibration is required or the sensor may need replacing. In alternative embodiments, the out-of-range limit is set at higher or lower values depending on the range of sensor sensitivities, the expected working life of the sensor, the range of acceptable measurements, and the like. In particular embodiments, the out-of range limit is applied to the sampled values. In other embodiments, the out-of-range limit is applied to the memory storage values.

In preferred embodiments, unstable signal alarm limits are set to detect when memory storage values change too much from one to another. The signal alarm limits are established similarly to the clipping limits described above for the interval values, but allow for a larger change in value since there is more time between memory storage values than between interval values. Re-calibration or replacement of the glucose sensor 12 is required once an unstable signal alarm is activated. In essence, the glucose monitor 100 has detected too much noise in the ISIG from the glucose sensor 12.

Each memory storage value is considered valid (Valid ISIG value) unless one of the following calibration cancellation events occurs: an unstable signal alarm (as discussed above), a sensor initialization event (as discussed above), a sensor disconnect alarm, a power on/off event, an out-of-range alarm (as discussed above), or a calibration error alarm. Only Valid ISIG values are used to calculate blood glucose levels by the glucose monitor 100 or post processor 200, as shown in FIG. 10. Once a calibration cancellation event occurs, the successive memory storage values are not valid, and therefore are not used to calculate blood glucose, until the glucose monitor 100 or post processor 200 is re-calibrated. FIG. 10 shows an explanatory computer screen in which cell P3 indicates a sensor disconnect alarm with the abbreviation "SeDi". As shown, blood glucose values do not appear in column K, titled "Sensor Value", and Valid ISIG values do not appear in column J until after the sensor is initialized, as indicated by the "ESI" flag in cell N17. One exception however, is the power on/off event. If the glucose monitor 100 is turned off for a short enough period of time, generally up to 30 minutes, the memory storage values are considered Valid ISIG values as soon as the power is turned back on. If the power is off for longer than 30 minutes, the glucose monitor must be re-calibrated before ISIG values are considered valid. Alternatively, the power may be off 30 minutes up to indefinitely and once the power is restored, the memory storage values are Valid ISIG values. The sensor disconnect alarm is activated when the glucose monitor 100 does not detect a signal. In preferred embodiments, when 2 or more out of 5 interval values collected within a given memory storage rate are less than 1.0 Nano-Amp, the disconnect alarm is triggered. In alternative embodiments, more or less values need be below a particular amperage to trigger the disconnect alarm depending of the acceptable range or sensor readings and the stability of the sensor signal. The remaining two calibration cancellation events, the calibration error and an alternative embodiment for the out-of-range alarm, are discussed in conjunction with the calibration process below.

Preferred embodiments are directed to calibration techniques that are used by either glucose monitors 100 during real-time measurements of one or more signals from the glucose sensor 12, or post processors 200 during post-processing of data that has been previously recorded and downloaded (as shown in FIG. 10).

To calibrate the glucose monitor 100, the calibration factor called a sensitivity ratio (SR) (blood glucose level/Valid ISIG value) is calculated for a particular glucose sensor 12. The SR is a calibration factor used to convert the Valid ISIG value (Nano-Amps) into a blood glucose level (mg dl or mmol/l). In alternative embodiments, the units for the SR may vary depending on the type of signal available from the sensor (frequency, amplitude, phase shift, delta, current, voltage, impedance, capacitance, flux, and the like), the magnitude of the signals, the units to express the characteristic being monitored, or the like.

Figure 11:
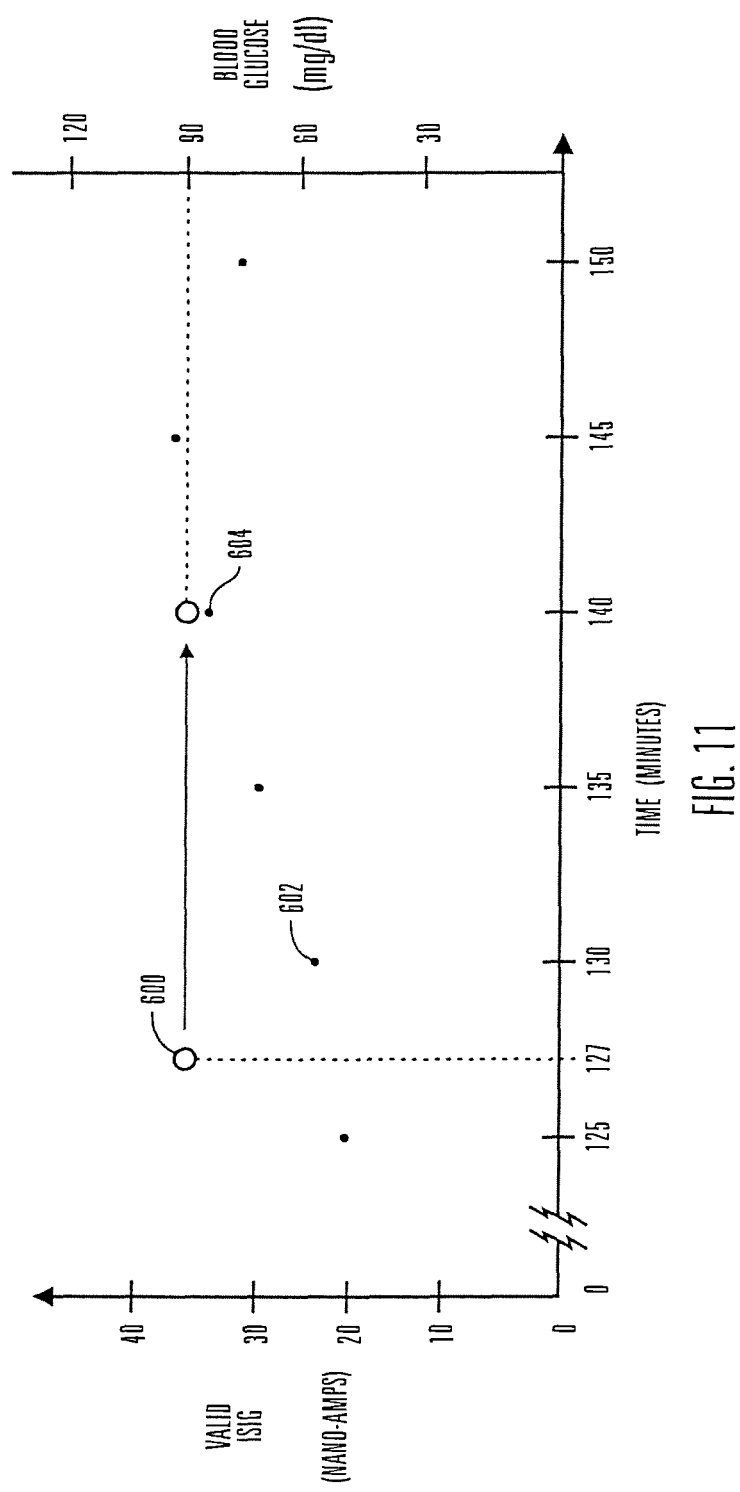
FIG. 11 is a chart illustrating the pairing of a blood glucose reference reading with glucose monitor data.

In preferred embodiments, the user obtains a blood glucose reference reading from a common glucose meter, or another blood glucose measuring device, and immediately enters the blood glucose reference reading into the glucose monitor 100. The blood glucose reference reading is assumed to be accurate and is used as a reference for calibration. The glucose monitor 100, or a post processor 200, must temporally correlate the blood glucose reference reading with a Valid ISIG value to establish a paired calibration data point. Since the glucose level in the interstitial body fluid tends to lag behind the blood glucose level, the glucose monitor 100 or post processor 200 applies a delay time and then pairs the blood glucose reference reading with a Valid ISIG value as shown in FIG. 11. In preferred embodiments, an empirically derived 10 minute delay is used. Since Valid ISIG values are averaged and stored every 5 minutes, the glucose monitor 100 correlates the blood glucose reference reading with the third Valid ISIG stored in memory after the blood glucose reference reading is entered (resulting in an effective delay of 10 to 15 minutes). FIG. 11 illustrates an example, in which a blood glucose reference reading 600 of 90 mg/dl is entered into the glucose monitor 100 at 127 minutes. The next Valid ISIG value 602 is stored at 130 minutes. Given a 10 minute delay, the glucose reference reading 600 is paired with the Valid ISIG value 604 which is stored at 140 minutes with a value of 30 Nano-amps. Note that two numbers are needed to establish one paired calibration data point, a blood glucose reference reading and a Valid ISIG.

Other delay times may be used depending on the user's metabolism, the response time of the sensor, the delay time required for the glucose meter to calculate a reading and for the reading to be entered into the glucose monitor 100, the type of analyte being measured, the tissue that the sensor is placed into, environmental factors, whether the previous glucose Valid ISIG value (or the trend of the Valid ISIG values) was higher or lower than current Valid ISIG value, or the like. Once paired calibration data is available, the appropriate calibration process may be applied dependent on how many paired calibration data points are available since the last calibration, the total period of time that the glucose sensor 12 has been in use, and the number of times the glucose sensor 12 has been calibrated.

In preferred embodiments, blood glucose reference readings are entered into the glucose monitor 100 periodically through out each day of use. Preferably calibration is conducted immediately after the initialization/stabilization of a glucose sensor 12 and once a day thereafter. However, calibration may be conducted more or less often depending on whether a glucose sensor 12 has been replaced, whether a calibration cancellation event has occurred, the stability of the glucose sensor 12 sensitivity over time, or the like.

In preferred embodiments, blood glucose reference readings are collected several times per day but a new calibration factor is calculated only once per day. Therefore, typically more than one paired calibration data point is collected between calibrations. In alternative embodiments, the glucose monitor is calibrated every time a new paired calibration data point is collected.

Figure 13:
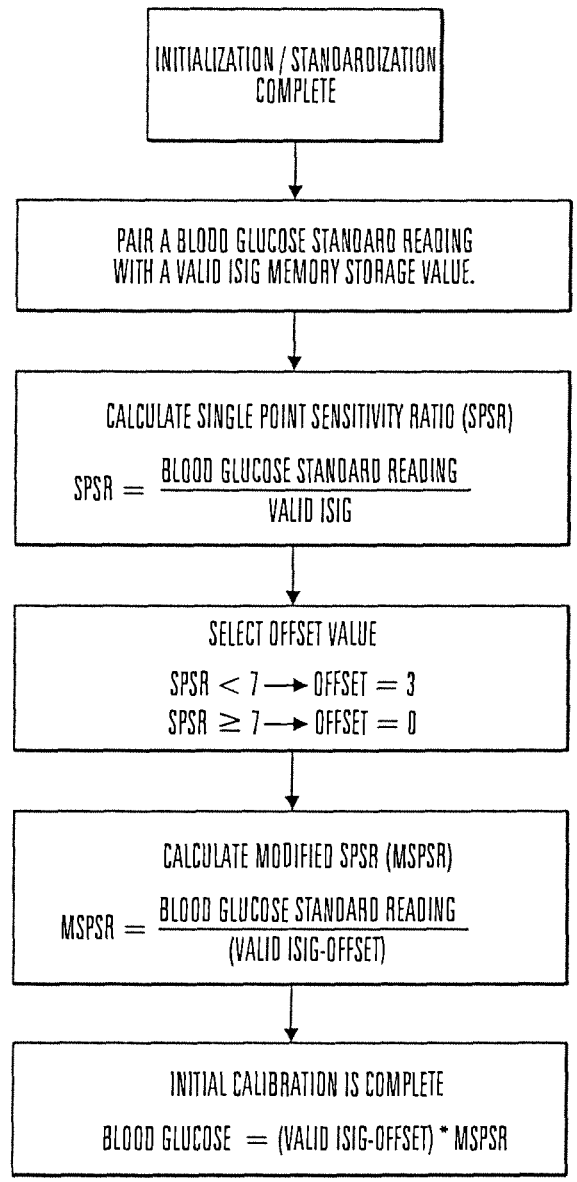
FIG. 13 is a block diagram of a single-point calibration technique.
Figure 15:
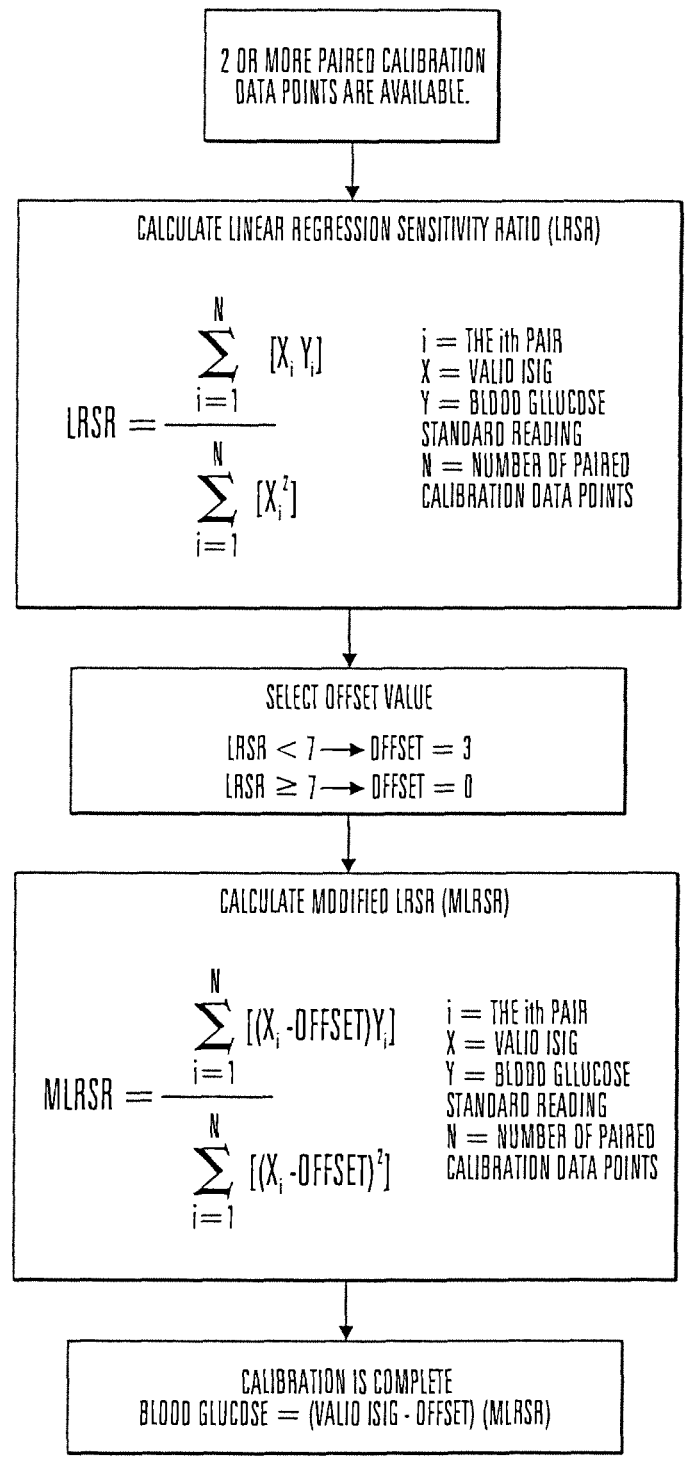
FIG. 15 is a block diagram of a linear regression calibration technique.

Preferred embodiments use a single-point calibration technique (shown in a block diagram of FIG. 13) to calculate the SR when only one paired calibration data point is available, such as immediately after initialization/stabilization. And a modified linear regression technique (shown in a block diagram in FIG. 15) is used when two or more paired calibration data points are available. Particular embodiments use a single-point calibration technique whether or not more than one paired calibration data point is available.

Figure 12:
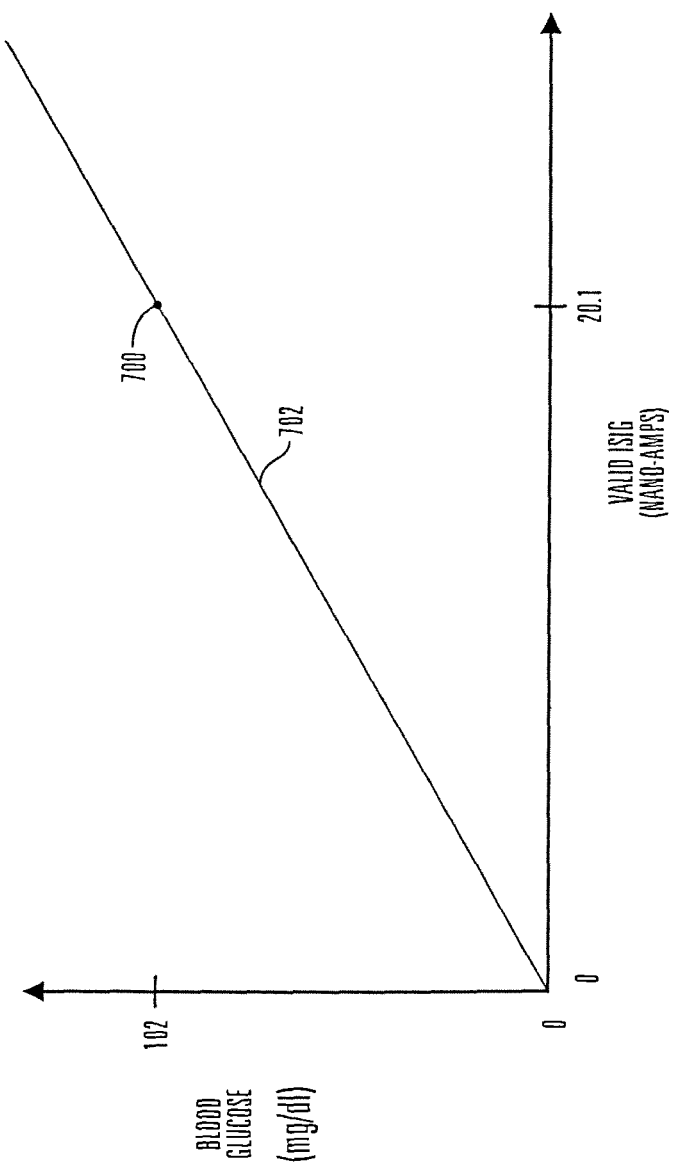
FIG. 12 is a chart illustrating an example of a single-point calibration.

A single-point calibration equation is based on the assumption that the Valid ISIG will be 0 when the blood glucose is 0. As shown in FIG. 12, a single paired calibration point 700 is used with the point (0,0) to establish a line 702. The slope of the line from the origin (0,0) and passing through the single paired calibration point 700 is the single-point sensitivity ratio (SPSR). The single-point calibration equation to calculate the calibration factor SPSR is as follows:

$$SPSR = \frac{\text{Blood Glucose Reference Reading}}{\text{Valid } ISIG}$$

where SPSR=a Single-Point Sensitivity Ratio.

Therefore, the calibrated blood glucose level is,

Blood Glucose Level=Valid ISIG*SPSR.

As an example, using the values of 20.1 Nano-Amps and 102 mg/dl from the paired calibration data point shown in FIG. 12, the calculation of SPSR is:

SPSR=102/20.1=5.07 mg/dl per Nano-amp.

To continue the example, once the calibration is complete, given a glucose sensor reading of 15.0 Nano-Amps, the calculated blood glucose level is:

Blood Glucose Level=15.0*5.07=76.1 mg/dl.

Additionally, particular embodiments use an offset value in a calibration equation to compensate for the observation that more sensitive glucose sensors 12 (i.e. glucose sensors 12 that generate higher ISIG values compared to other glucose sensors 12 at the same blood glucose level, which result in lower SR values) often have a less linear performance at very high blood glucose levels when compared to glucose sensors 12 with lower sensitivity (and therefore relatively higher SR values). If the SPSR for a particular glucose sensor 12, as calculated above, is less than a sensitivity threshold value, then a modified SPSR (MSPSR) is calculated using an offset value included in a modified single-point calibration equation. In preferred embodiments, the threshold value is 7. When the initial calculation of the SPSR (shown above) is less than 7, an offset value of 3 is used to calculate the MSPSR. If the initial calculation of SPSR yields a value of 7 or greater, then the offset value is 0. Thus, the calibration factor (MSPSR) is calculated using the offset value in the modified single-point calibration equation, as follows:

$$MSPSR = \frac{\text{Blood Glucose Reference Reading}}{(\text{Valid } ISIG\text{-offset})}$$

Therefore, the calibrated blood glucose level is,

Blood Glucose Level=(Valid ISIG−offset)*MSPSR.

Continuing the above example since the SPSR is 5.07, which is less than 7, the sensitivity ratio is recalculated using the MSPSR equation as:

MSPSR=102/(20.1−3)=5.96 mg/dl per Nano-amp.

And given a glucose sensor reading of 15.0 Nano-Amps after calibration the calculated blood glucose level is:

Blood Glucose Level=(15.0−3)*5.96=71.5 mg/dl.

In another example, given a blood glucose reference reading of 95 from a typical blood glucose meter and a Valid ISIG value of 22.1, the resulting SPSR is 95/22.1=4.3. Since SR<7, the offset=3. Therefore, the MSPSR is 95/[22.1-3]=5.0. Note that when the SPSR is greater than or equal to 7 the offset value is 0 and therefore the MSPSR=SPSR.

In alternative embodiments, the offset value is eliminated from the equation for calculating the blood glucose value as follows:

Blood Glucose Level=Valid ISIG*MSPSR.

The threshold value of 7 and the associated offset of 3 have been empirically selected based on the characteristics observed from testing a particular type of glucose sensors 12, such as those described in U.S. Pat. No. 5,391,250 entitled "Method of Fabricating Thin Film Sensors", and U.S. Patent Application Ser. No. 60/121,655 filed on Feb. 25, 1999, entitled "Glucose Sensor Set", incorporated by reference herein. Other threshold values may be used in conjunction with other offset values to optimize the accuracy of the calculated MSPSR for various types of glucose sensors 12 and sensors used to detect other body characteristics. In fact, many threshold values may be used to select between many offset values. An example using two different threshold values (4 and 7) to select between three different offset values (5, 3 and 0) follows:

If the SPSR<4, then use an offset value of 5, else
if 4<=SPSR<7, then use an offset value of 3, else
if SPSR>=7 use an offset value of 0.

In preferred embodiments the MSPSR is compared to a valid sensitivity range to determine if the newly calculated MSPSR is reasonable. In order to identify potential system problems, a valid MSPSR range of 1.5 to 15 is employed. This range has been determined based upon valid glucose sensor sensitivity measurements made in-vitro. MSPSR values outside this range result in a calibration error alarm (CAL ERROR) to notify the user of a potential problem. Other valid sensitivity ranges may be applied depending on the types of sensors to be calibrated, the range of acceptable sensitivity levels for the various sensor types, the manufacturing consistency expected for the sensors, environmental conditions, how long the sensor has been in use, or the like.

Figure 14:
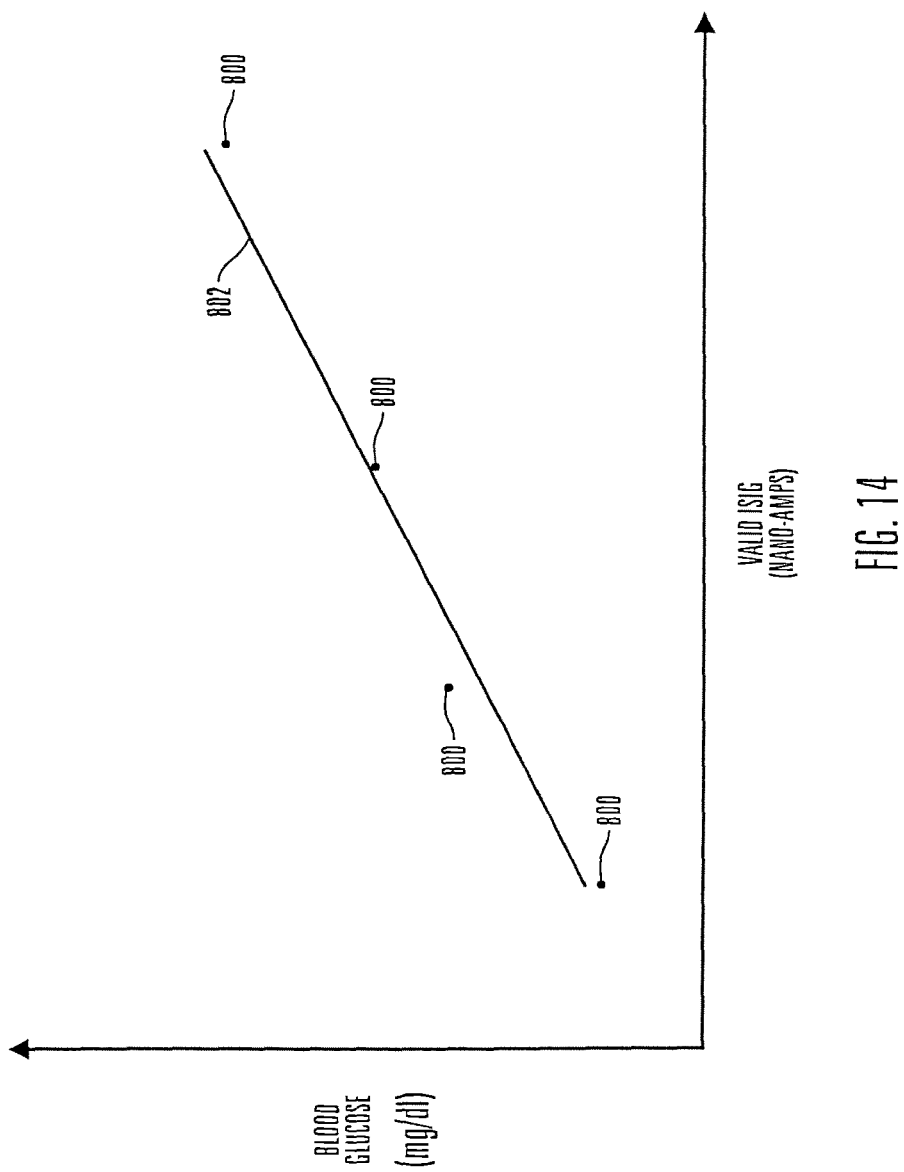
FIG. 14 is a chart illustrating an example of a linear regression calibration.

Preferred embodiments augment the single-point calibration technique using a modified linear regression technique (shown in a block diagram in FIG. 15) when more than one paired calibration data point is available. As shown in FIG. 14, the paired calibration data points 800 are linearly regressed by a least squares method to calculate the best fit straight line 802 correlated with paired calibration data points 800. The slope of the line resulting from the linear regression is the linear regression sensitivity ratio (LRSR) used as the calibration factor to calibrate the glucose monitor 100. The linear regression calibration equation is as follows:

$$LRSR = \frac{\sum_{i=1}^{N}[X_i Y_i]}{\sum_{i=1}^{N}[X_i^2]}$$

where $X_i$ is the ith Valid ISIG value of paired calibration data points, $Y_i$ is the ith Blood Glucose Reference Reading of paired calibration data points and, N is the total number of paired calibration data points used for calibration.

i is the identification number of a particular paired calibration data point.

Therefore, the calibrated blood glucose level is,

Blood Glucose Level=Valid ISIG*LRSR.

Note that this linear regression uses a fixed intercept of zero (in other words, when the Valid ISIG is 0 the blood glucose value is 0) and therefore the linear regression method estimates only one regression parameter, the slope. In alternative embodiments, other linear regression methods may be used that estimate additional regression parameters such as an offset value.

Additionally, particular embodiments use an offset value in a modified linear regression calibration equation. The purpose of the offset value, as described above for the single-point calibration, is to compensate for the observation that more sensitive glucose sensors 12 often have a less linear performance at very high blood glucose levels. If the LRSR for a particular glucose sensor 12, as calculated in the linear regression calibration equation above, is less than a sensitivity threshold value, then a modified linear regression sensitivity ratio (MLRSR) is calculated using an offset value included in a modified linear regression calibration equation. In preferred embodiments, the threshold value is 7. When the initial calculation of the LRSR is less than 7, an offset value of 3 is used to calculate the MLRSR. If the initial calculation of LRSR yields a value of 7 or greater, then the offset value is 0. Thus, the MLRSR is calculated using the offset value in the modified linear regression calibration equation, thus:

$$MLRSR = \frac{\sum_{i=1}^{N}[(X_i - \text{offset})Y_i]}{\sum_{i=1}^{N}(X_i - \text{offset})^2}$$

Therefore, the calibrated blood glucose level is,

Blood Glucose Level=(Valid ISIG−offset)*MLRSR.

Just as in the case of single-point calibration techniques described above, other threshold values may be used in conjunction with other offset values in the modified linear regression calibration equation to optimize the accuracy of the calculated MLRSR for various types of glucose sensors 12 and other characteristic sensors.

In preferred embodiments the MLRSR is compared to a valid sensitivity range to determine if the newly calculated MLRSR is reasonable. In order to identify potential system problems, a valid MLRSR range of 2.0 to 10.0 is employed. MLRSR values outside this range result in a calibration error alarm (CAL ERROR) to notify the user of a potential problem. As described above for the single-point calibration techniques, other valid sensitivity ranges may be applied.

In preferred embodiments, the glucose monitor data is linearly regressed over a 24 hour period (or window), and new sensitivity ratios are used for each 24 hour time period. In alternative embodiments, the time period may be reduced to only a few hours or enlarged to cover the entire monitoring period with the glucose sensor (i.e., several days—or even weeks with implanted sensors). In further embodiments, the time window may be fixed at a predetermined size, such as 24 hours, 12 hours, 6 hours, or the like, and the window is moved along over the operational life of the sensor.

In particular embodiments, paired calibration data points from measurements taken before the last calibration may be used to calculate a new sensitivity ratio. For example, to calibrate the glucose monitor every 6 hours, a paired calibration data point is established every 6 hours. And the linear regression technique described above is executed using 4 paired calibration data points, the most recently acquired point and points from 6, 12 and 18 hours before. Alternatively, the number of paired calibration data points used in the calibration may be as few as one or as large as the total number of paired calibration data points collected since the glucose sensor was installed. In alternative embodiments, the number of paired calibration data points used in a calibration equation may grow or shrink during the life of the glucose sensor due to glucose sensor anomalies.

In still other embodiments, the decay characteristics of the glucose sensor 12 over time may be factored into the equation to account for typical degradation characteristics of the glucose sensor 12 due to site characteristics, enzyme depletion, body movement, or the like. Considering these additional parameters in the calibration equation will more accurately tailor the calibration equation used by the glucose monitor 100 or post processor 200. In particular embodiments, other parameters may be measured along with the blood glucose such as, temperature, pH, salinity, and the like. And these other parameters are used to calibrate the glucose sensor using non-linear techniques.

Figure 16:
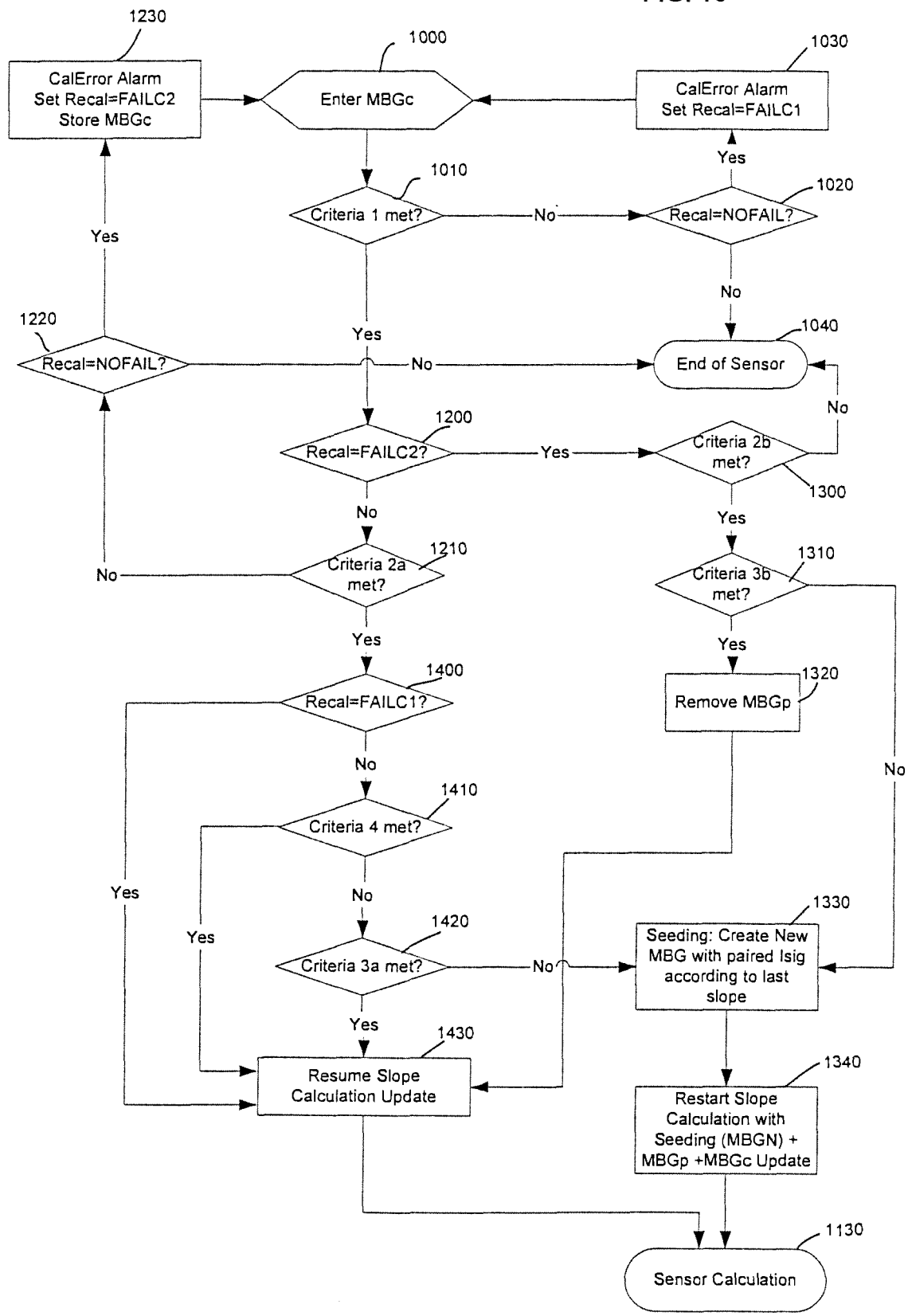
FIG. 16 is a flowchart of a self-adjusting calibration technique in accordance with an embodiment of the present invention.

In a preferred embodiment, real-time calibration adjustment can be performed to account for changes in the sensor sensitivity during the lifespan of the glucose sensor 12 and to detect when a sensor fails. FIG. 16 (in conjunction with FIGS. 17 and 18) describes the logic of a self-adjusting calibration technique to adjust the calibration formula or detect a sensor failure in accordance with an embodiment of the present invention.

At block 1000, the user obtains a blood glucose reference from a common glucose meter, or another blood glucose measuring device, and immediately enters the blood glucose reference reading into the glucose monitor 100. For every meter blood glucose entry, an instantaneous calibration check is performed and compared to an expected range of the value of the calibration check, as in block 1010. In preferred embodiments, the Calibration Factor current is calculated (i.e. CFc=Meter BG/current ISIG value) to determine if the CFc (Calibration Factor current) ratio is between 1.5 to 12 ("Criteria 1"), a minimum criteria for an accurate ISIG value. If data is outside this range, raising the likelihood of a sensor failure or incorrect determination/entry of the meter BG value, a Cal Error alarm is triggered at block 1030 and the Recalibration Variable (Recal), which is originally set at NOFAIL is changed to FAILC1. At this point, another blood glucose reference reading is requested and entered into the glucose monitor 100 to determine whether there was indeed a sensor failure or the Meter Blood Glucose value was incorrectly inputted. The previous MBGc that generated the error can be thrown out completely. If Criteria 1 is again not satisfied at block 1010, an end of the sensor life message will be generated at block 1040 since then the Recal variable would be recognized as FAILC1 at block 1020. However, if Criteria 1 is met at block 1010, then the logic proceeds to block 1200, where a check of the Recal Variable is made to see if Recal variable is not equal to FAILC2. The Recal variable is set to FAILC2 only if Criteria 2a is not met, which will be discussed below. Given that the Recal variable at this point would only be set a NOFAIL or FAILC1, the logic proceeds to block 1210.

At block 1210, a check is performed if the existing calibration slope estimation (Previous Estimated Slope or PES) is much different from the instantaneous calibration check (CFc) performed using the new meter blood glucose value. A significant difference can indicate a sensor failure. In the preferred embodiment, a difference between the previous estimated slope (PES) and the current calibration check (CFc) in terms of percentage (threshold 1) and mg/dl (threshold 2) is performed. Threshold 1 and 2 can be set depending on the particular sensor characteristics. An example of checking the changes between the PES and CFc is as follows:

$$Abs(1-PES/CFc)*100=\text{Threshold 1 and}$$

$$Abs(CFc-PES)*\text{Isig}=\text{Threshold 2}$$

If the percentage and/or absolute difference exceeds threshold 1 and/or threshold 2 (collectively "Criteria 2a"), then depending on the Recal variable (at block 1220), either trigger an end of sensor message at block 1040 (if the Recal variable is equal to FAILC1 or FAILC2 at block 1220) or a Cal Error alarm will be generated at block 1230 (if the Recal variable is equal to NOFAIL at block 1220). If a Cal Error alarm is generated at block 1230, the Recal variable is set to FAILC2, the current meter blood glucose reading will be stored as MBGp (Meter Blood Glucose previous), and another blood glucose reference is requested and entered into the glucose monitor 100 (as MBGc) at block 1000. By requesting a new meter blood glucose reading, a comparison can be made between the last meter blood glucose reading stored at block 1230 and the new meter blood glucose reading entered at block 1000 to determine whether there was a sensor failure. The logic follows the same paths as described above after block 1000 until the logic reaches block 1200. At block 1200, since Recal variable is now set to FAILC2 at block 1230, the difference between the previous calibration check (CFp), which generated the FAILC2 alert, and the current calibration check (CFc) is performed at block 1300. In preferred embodiments, the difference between the previous calibration check and the current calibration check in terms of percentage (threshold 1) and mg/dl (threshold 2) is performed. In addition, a check is performed on whether there has been a directional change between the CFp and CFc (collectively "criteria 2b"). An example of criteria 2b is as follows:

$$Abs(1-CFp/CFc)*100=\text{Threshold 1 and}$$

$$Abs(CFc-CFp)*\text{Isig}=\text{Threshold 2 and}$$

$$(CFp-PES)*(CFc-CFp)>0$$

If the percentage and absolute difference exceeds threshold 1 and threshold 2, and there is no directional change in the slope with the second blood glucose meter reading, then an end of sensor message will be triggered at block 1040. If criteria 2b is met, then the logic proceeds to block 1310. At block 1310, the logic then determines whether the difference between the previous value and the current value was due to a change in sensitivity of the sensor or whether the reading is merely noise. In the preferred embodiment, the determination of change in sensitivity versus noise is made by using Criteria 3b. Criteria 3b compares the difference between (the previous estimated slope (PES) and the current calibration check (CFc)) and (the previous calibration check (CFp) versus the current calibration check (CFc)) at block 1420. For example:

$$Abs(PES-CFc)<Abs(CFp-CFc)$$

Figure 17A:
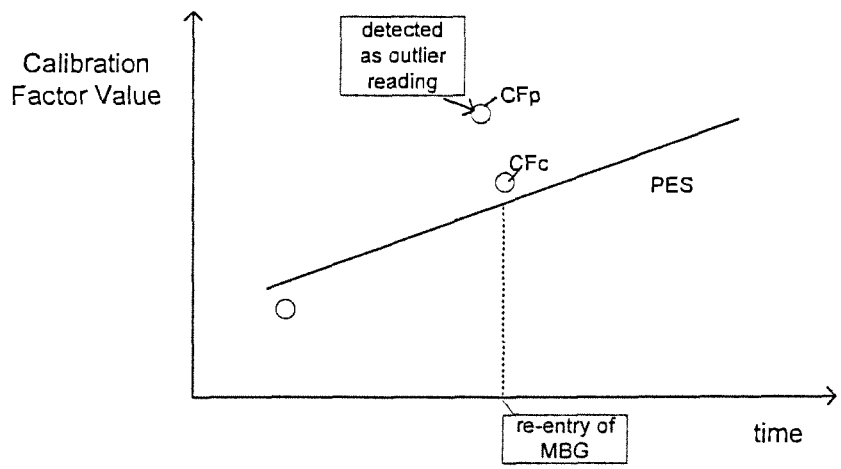
FIGS. 17a and 17b are charts illustrating an example of the self-adjusting calibration technique in accordance with FIG. 16.

As illustrated in FIG. 17a, if the difference between the estimated slope (PES) and the current calibration check (CFc) is less than the difference between the previous calibration check (CFp) and the current calibration check (CFc), criteria 3b will be met, indicating that the previous CFp is an outlier reading (i.e. an anomaly). Then, the MBGp (Meter Blood Glucose previous) is removed at block 1320 and only the MBGc paired with a valid ISIG is used in the slope calculation, which is resumed at block 1430 and applied in interpreting the sensor readings at block 1130.

Figure 17B:
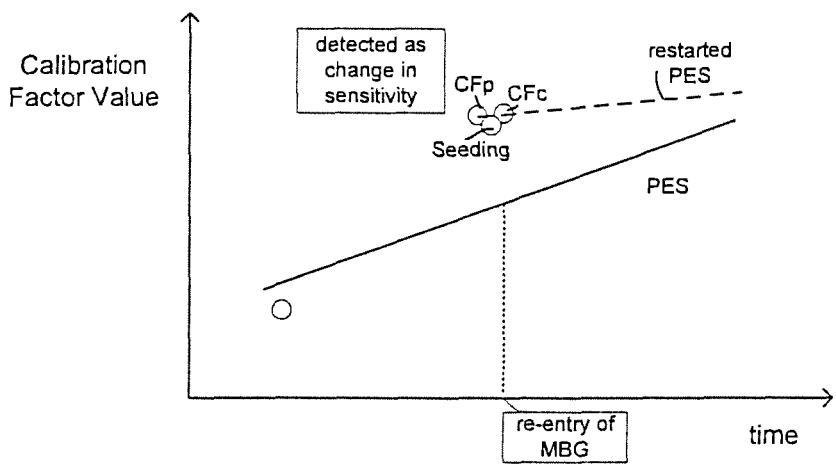

As illustrated in FIG. 17b, if criteria 3b shows that difference between the estimated slope (PES) and the current calibration check (CFc) is greater than the difference between the previous calibration check (CFp) and the current calibration check (CFc), criteria 3b would not be met, indicating a change in sensor sensitivity. The slope calculation is then fine-tuned by creating a new (artificial) meter blood glucose value (MBGN) with a paired ISIG according to the last slope (Seeding) at block 1330. Using the new paired MBG (MBGN) with the paired MBGp and MBGc, the slope calculation is restarted (or reset) at block 1340, as seen in FIG. 17b. The sensor calculation is then performed using the new slope calculation at block 1130. By resetting the slope calculation, the slope calculation can thus be modified automatically to account for changes in sensor sensitivity.

Continuing the logic from block 1210, if the percentage and/or absolute difference between the PES and CFc is within threshold 1 and/or threshold 2 at block 1210, indicating a valid calibration, the Recal variable is again checked at block 1400. If the Recal variable is equal to FAILC1 (indicating that the meter BG was checked twice), any fine-tuning determination is skipped and the MBGc paired with a valid ISIG is used to update the slope calculation at block 1430 and applied in interpreting the sensor readings at block 1130. If the Recal Variable is not equal to FAILC1, then the logic will decide whether fine-tuning the slope calculation is needed at blocks 1410 and 1420. In the preferred embodiments, the decision to fine-tune is first made by comparing the percentage and/or absolute difference between the PES and CFc (as done in block 1210) with a threshold 3 and/or a threshold 4 ("Criteria 4") at block 1410. For example:

$$Abs(1-PES/CFc)*100<\text{Threshold 3 and}$$

$$Abs(CFc-PES)*ISIG<\text{Threshold 4}$$

Again, threshold 3 and 4 can be determined based on the particular sensor characteristics. If the percentage and/or absolute difference between the PES and CFc is less than threshold 3 and/or threshold 4 at block 1410 (i.e. Criteria 4 met), then the slope calculation can simply be updated with the new MBGc and paired ISIG value at block 1430 and applied in interpreting the sensor readings at block 1130.

On the other hand, if the Criteria 4 is not met at block 1410, the logic then determines at block 1420 whether the difference between the expected value and the current value was due to a change in sensitivity of the sensor or whether the reading is merely noise. In the preferred embodiment, the determination of change in sensitivity versus noise is made by using Criteria 3a. Criteria 3a compares the difference between (the previous estimated slope (PES) and the previous calibration check (CFp)) and (the current calibration check (CFc) versus the previous calibration check (CFp)) at block 1420. For example:

$$Abs(PES-CFp)<Abs(CFc-CFp)$$

Figure 18A:
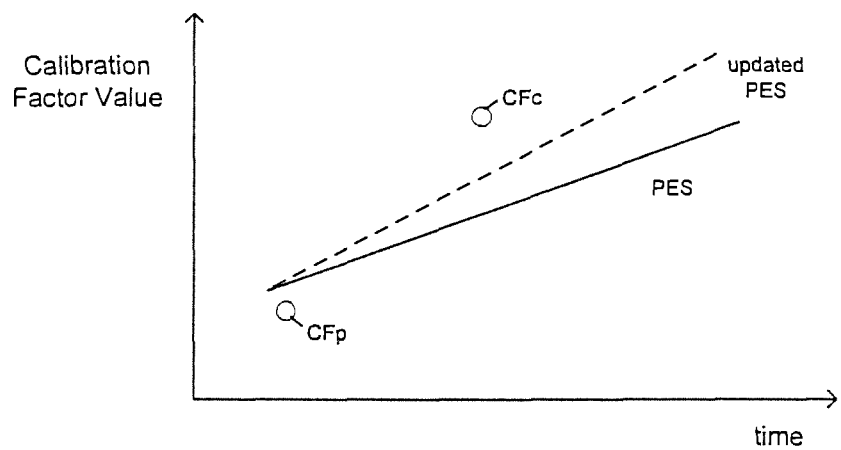
FIGS. 18a and 18b are further charts illustrating an example of the self-adjusting calibration technique in accordance with FIG. 16.

As seen in FIG. 18a, if the difference between the estimated slope (PES) and the previous calibration check (CFp) is less than the difference between the current calibration check (CFc) and the previous calibration check (CFp), criteria 3a will be met, indicating that the error between the predicted value and the actual value for the CFc was due to noise in previous calibrations or beginning of a change in sensor sensitivity which will be picked up at the next calibration performance. The slope calculation is then simply updated with the new paired blood glucose entry (MBGc) at block 1430 and applied in interpreting the sensor readings at block 1130.

Figure 18B:
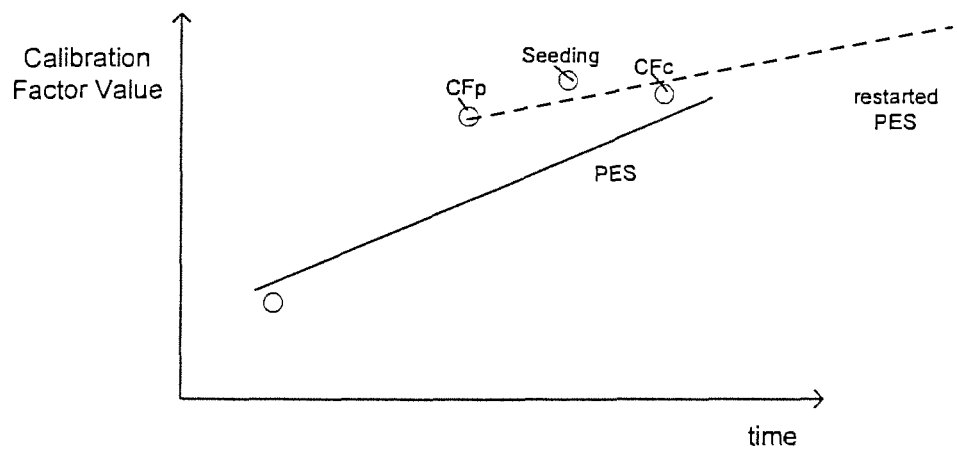

As seen in FIG. 18b, if criteria 3a shows that difference between the estimated slope (PES) and the previous valid calibration check is greater than the difference between the previous valid calibration check (CFp) and the current calibration check (CFc), criteria 3b would not be met, indicating a change in the sensor sensitivity and fine tuning is performed. Typically, fine tuning is performed when two MBG entry in succession indicate a change in slope. The slope calculation is fine-tuned by creating a new (artificial) meter blood glucose value (MBGN) with a paired ISIG according to the last slope (Seeding) at block 1330. Using the new paired MBG (MBGN) with the paired MBGp and MBGc, the slope calculation is restarted (or reset) at block 1340, as seen in FIG. 18b. The sensor calculation is then performed using the new slope calculation at block 1130. Again, by resetting the slope calculation, the slope calculation can thus be modified automatically to account for changes in sensor sensitivity.

Alternative Calibration Techniques

Although the above description described the primary calibration techniques in the preferred embodiments, many modifications can be made to the above described calibration techniques. For example, in alternative embodiments, the calibration factor may be calculated by first using a single-point technique to calculate the MSPSR for each paired calibration data point and then averaging them together, either unweighted or weighted by temporal order of by elapsed time. In other alternative embodiments, other straight line curve fitting techniques may be used to calculate a slope to be used as the SR. In additional alternative embodiments, other non-regressive curve fitting techniques may be used to generate equations that express the blood glucose level relative to the Valid ISIG. The equations may be polynomial, parabolic, hyperbolic, asymptotic, logarithmic, exponential, Gaussian or the like. In these embodiments, the SR is not a single value (such as a slope) but rather an equation representing a curve that is used to convert the Valid ISIG from the glucose sensor 12 to a blood glucose value in the glucose monitor 100 or a post processor 200. In addition, in using a more robust formula for approximating the slope, the different ISIG can be given different weights, as to weigh the more recent ISIGs more than the older ISIGs. For example where there are contiguous 8 ISIGs (i.e. n=8) are available:

$$\text{Filtered } ISIG_{(i)} = \frac{\sum_{i=i-7}^{i} W_i * RawISIGi}{\sum_{i=i-7}^{i} W_i}$$

where Weights (i)=$W_i$=[0.9231 0.7261 0.4868 0.2780 0.1353 0.0561 0.0198 0.0060]

When contiguous 8 ISIGs are not available (n<8) (i.e. after initialization or after triple skips in transmission, the weighting formula would be as follows:

$$\text{Filtered } ISIG_{(i)} = \frac{\sum_{i=i-(n-1)}^{i} W_i * RawISIGi}{\sum_{i=i-(n-1)}^{i} W_i},$$

where n=number of contiguous ISIGs.

Once all paired meter BGs/ISIGs (Pairing weights) have been weight distributed, the modified regression equation shall generate the slope. In a preferred alternative embodiment, a Gaussian function $$\frac{1}{\sqrt{2\pi}} e^{\frac{-x^2}{2\sigma^2}}$$

is used to curve fit the sensor data, including the weighting functions, the Gaussian Slope is calculated using a modified regression model such as:

$$\text{Gaussian\_slope} = \frac{\sum PW_i \times (\text{Filtered\_Isig}) \times MBG_i}{\sum PW_i \times (\text{Filtered\_Isig})^2}$$

where i=number of pairs in Gaussian buffer and $$PW_i = e^{\frac{-(Ti-Tc)^2}{2\sigma^2}}$$

where Tc is the current time, Ti is Paired MBG/Filtered ISIG Times and σ=15 hours (or 180 records, which is the width of the Gaussian profile).

Alternatively, the above calculation can use an exponential slope calculation rather than a Gaussian calculation. The Exponential Slope is calculated using a modified regression model such as:

$$\text{Exponential\_slope} = \frac{\sum PW_i \times (\text{Filtered\_Isig}) \times MBG_i}{\sum PW_i \times (\text{Filtered\_Isig})^2}$$

where Δt=elapsed time, σ=hours of time evaluated (e.g. 5 hours, 7 hours, 15 hours, etc) and $$PW_i = e^{\frac{-(\Delta t)}{\sigma}}$$

As discussed, preferred embodiments utilize a least squares linear regression equation to calibrate the glucose monitor 100 or post-processor 200 to analyze the sensor data. However, alternative embodiments may utilize a multiple component linear regression, or equations with more variables than just the paired calibration data points, to account for additional calibration effecting parameters, such as environment, the individual user's characteristics, sensor lifetime, manufacturing characteristics (such as lot characteristics), deoxidization, enzyme concentration fluctuation or degradation, power supply variations, or the like. Still other alternative embodiments may utilize singular and multiple, non-linear regression techniques.

In preferred embodiments, after the first calibration is performed on a particular glucose sensor 12, subsequent calibrations employ a weighted average using a sensitivity ratio (SPSR, MSPSR, LRSR, or MLRSR) calculated from data collected since the last calibration, and previous sensitivity ratios calculated for previous calibrations. So the initial sensitivity ratio (SR1) is calculated immediately after initialization/stabilization using a paired calibration data point and is used by the glucose monitor 100 or the post processor 200 until the second sensitivity ratio (SR2) is calculated. The second sensitivity ratio (SR2) is an average of SR1 and the sensitivity ratio as calculated using the paired calibration data points since the initial calibration (SRday1). The equation is as follows:

$$SR2 = \frac{(SR1 + SRday1)}{2}$$

The third sensitivity ratio (SR3) is an average of SR2 and the sensitivity ratio as calculated using the paired calibration data points since the second calibration (SRday2). The equation is as follows:

$$SR3 = \frac{(SR2 + SRday2)}{2}$$

The sensitivity ratios for successive days use the same format, which is expressed below in generic terms:

$$SR_n = \frac{(SR_{(n-1)} + SRday_{(n-1)})}{2}$$

where $SR_n$ is the new sensitivity ratio calculated at the beginning of time period, n, using data from time period (n−1), to be used by a real time glucose monitor 100, to convert Valid ISIGs to blood glucose readings throughout time period, n.

$SR_{(n-1)}$ is the previous sensitivity ratio calculated at the beginning of time period, n−1, using data from time period (n−2).

$SRday_{(n-1)}$ is the sensitivity ratio calculated using paired calibration data points collected since the last calibration.

Alternatively, the previous sensitivity ratios may be ignored and the SR is calculated using only the paired calibration data points since the last calibration. Another alternative is to equally average all previous SRs with the latest SR calculated using only the paired calibration data points since the last calibration. In alternative embodiments, the paired calibration data points are used to establish an equation for a curve representing SR over time. The curve is then used to extrapolate SR to be used until the next paired calibration data point is entered.

In embodiments that use a post processor 200 to evaluate the sensitivity ratio, the sensitivity ratio is calculated using paired calibration data points over a period of time since the last calibration and is not averaged with previous SRs. The sensitivity ratio for a period of time can then be applied to the same period of time over which the paired calibration data points were collected. This is more accurate than the real-time case described above for the glucose monitor 100 because, in the real-time case, sensitivity ratios from a previous time period must be used to calculate the blood glucose level in the present time period. If the sensitivity ratio has changed over time, the calculation of blood glucose using an old sensitivity ratio introduces an error.

In particular embodiments, once calibration is complete, Valid ISIG values are converted to blood glucose readings based on a particular version of the sensitivity ratio, and the resulting blood glucose readings are compared to an out-of-range limit. If the resulting calculated blood glucose level is greater than a maximum out-of-range limit of 200 nAmps, the out-of-range alarm is activated. This is a calibration cancellation event, therefore, ISIG values are no longer valid once this alarm is activated. The blood glucose readings are either not calculated, or at least not considered reliable, until the glucose monitor 100 or post processor 200 is re-calibrated. The user is notified of the alarm and that re-calibration is needed. In alternative embodiments, higher or lower maximum out-of-range limits may be used depending on the sensor characteristics, the characteristic being measured, the user's body characteristics, and the like. In particular embodiments, a minimum out-of-range limit may be used or both a maximum and a minimum out-of-range limits may be used. In other particular embodiments, the out-of-range limits do not cause the blood glucose readings to become invalid and/or re-calibration is not required; however, an alarm could still be provided. In additional particular embodiments, more than one ISIG value must exceed an out-of-range limit before an alarm is activated of a calibration cancellation event is triggered. The ISIG values that are out-of-range are not used to display a blood glucose value.

In alternative embodiments, calibration is conducted by injecting a fluid containing a known value of glucose into the site around the glucose sensor set 10, and then one or more glucose sensor readings are sent to the glucose monitor 100. The readings are processed (filtered, smoothed, clipped, averaged, and the like) and used along with the known glucose value to calculate the SR for the glucose sensor 12. Particular alternative embodiments, use a glucose sensor set of the type described in U.S. Pat. No. 5,951,521 entitled "A Subcutaneous Implantable Sensor Set Having the Capability To Remove Or Deliver Fluids To An Insertion Site".

In other alternative embodiments, the glucose sensor 12 is supplied with a vessel containing a solution with a known glucose concentration to be used as a reference, and the glucose sensor 12 is immersed into the reference glucose solution during calibration. The glucose sensor 12 may be shipped in the reference glucose solution. As described above, the glucose sensor readings are used to calculate a sensitivity ratio given the known glucose concentration of the solution.

In another alternative embodiment, the glucose sensors 12 are calibrated during the manufacturing process. Sensors from the same manufacturing lot, that have similar properties, are calibrated using a sampling of glucose sensors 12 from the population and a solution with a known glucose concentration. The sensitivity ratio is provided with the glucose sensor 12 and is entered into the glucose monitor 100 or the post processor 200 by the user or another individual.

In addition, although the preferred logic of FIG. 18 described specific operations occurring in a particular order, in alternative embodiments, certain of the logic operations may be performed in a different order, modified, or removed and still implement the preferred embodiments of the present invention. Moreover, steps may be added to the above described logic and still conform to the preferred embodiments. For example, although in the preferred embodiment of FIG. 16, the Recal variable is never reset to no fail, potentially, an additional step of can be added to reset the Recal variable to no fail if no cal error alarms are triggered after a predetermined number of calibrations.

Figure 19:
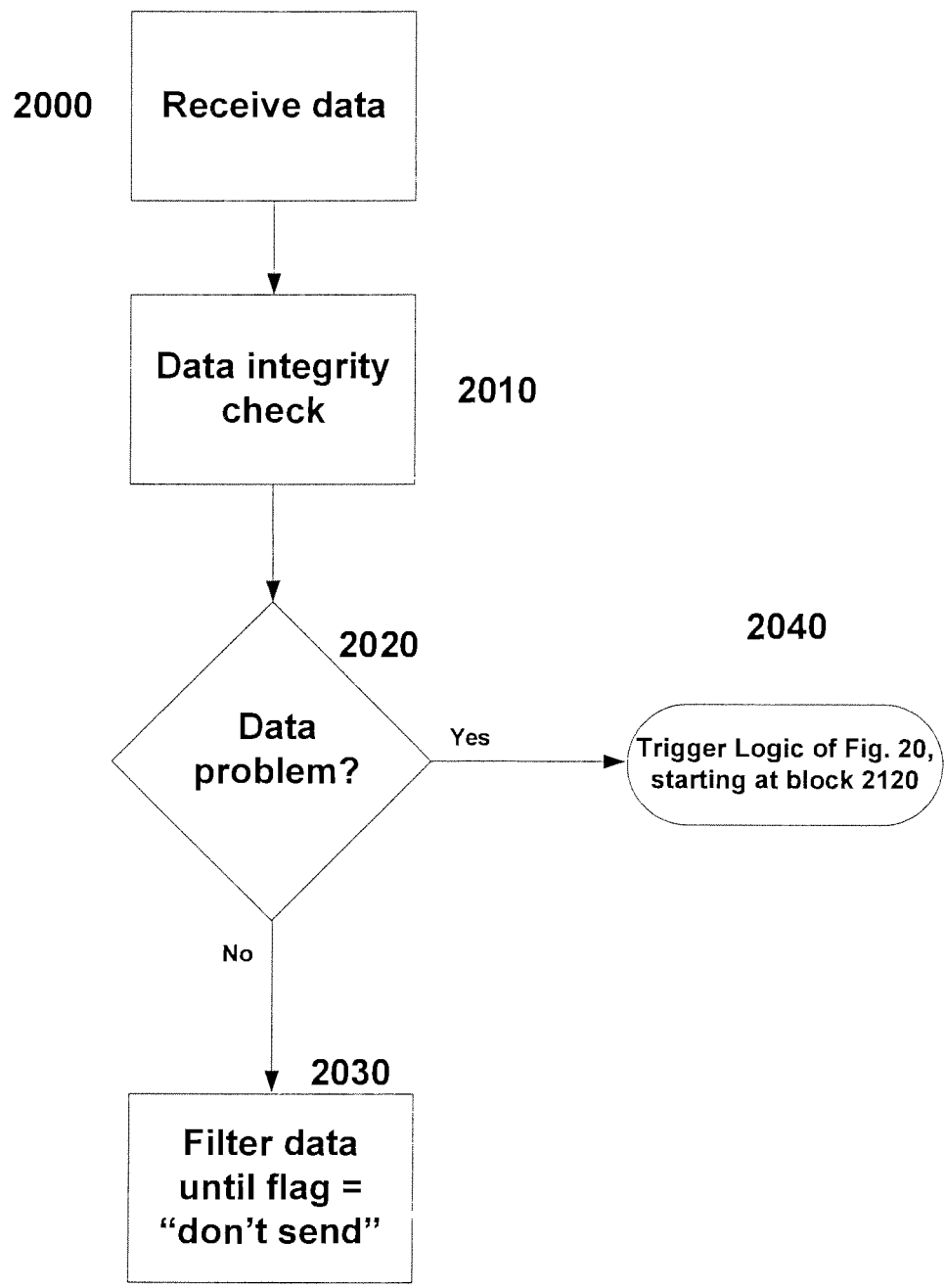
FIG. 19 is shows a generalized flow diagram for verifying data integrity according to an embodiment of the present invention.

According to embodiments of the present invention, further modifications to the previously described techniques may be made to provide additional assurance of the accuracy of the ISIG values. For example, FIG. 19 shows a generalized flow diagram for verifying the integrity of the ISIG values and filtering the ISIG values. The integrity check and filtering techniques described in FIG. 19 can be used in addition to or in replacement of the clipping limits and Gaussian filtering described previously. In addition, while FIG. 19 describes how the sensor can apply both an integrity check and filtering to the received ISIG values in series, in alternative embodiments, the integrity check or filtering can be performed independently, in parallel, or in exclusion of one another.

At step 2000, ISIG values are received from a sensor, such as the glucose sensor 12, for example. The ISIG values may undergo some pre-processing to derive a single ISIG value for a specified length of time. Thus, the ISIG values at step 2000 can be average ISIG values at periodic intervals as described previously (e.g., with regards to FIG. 5a-c). In particular embodiments, a 5 min ISIG value is used, but in alternative embodiments, the ISIG interval value can be any value including 1 min, 3 min, 10 min, etc.

At step 2010, the integrity of the data is verified. Thus, ISIG values received from the sensor are evaluated to determine if the ISIG values are accurate and usable or if the ISIG values are inaccurate and unusable. The step 2010 will be described in more detail with regards to FIG. 20.

At step 2020, a decision is made regarding the integrity of the data. If the data is accurate and usable, filtering is performed on the data to derive the glucose values corresponding to the ISIG values. The filtering process after the integrity check is described in greater detail below. If the data is inaccurate and unusable, the process proceeds to step 2040 and several things may occur. For example, the sensor may be shut down, data verification may be stopped, and/or the filter data flag may be set to "don't send." An embodiment of the logic of 2040 is described with respect to FIG. 20 starting at block 2120.

At step 2030, data may be sent to a filter as long as a filter flag is not equal to "don't send" or until some other mechanism (e.g., Cal Error) determines that data should not or can no longer be sent to a filter. The send data step 2030 may proceed as long as the data integrity verification step 2010 verifies that there are no anomalies in the data received that would warrant a shut down of the sensor.

Figure 20:
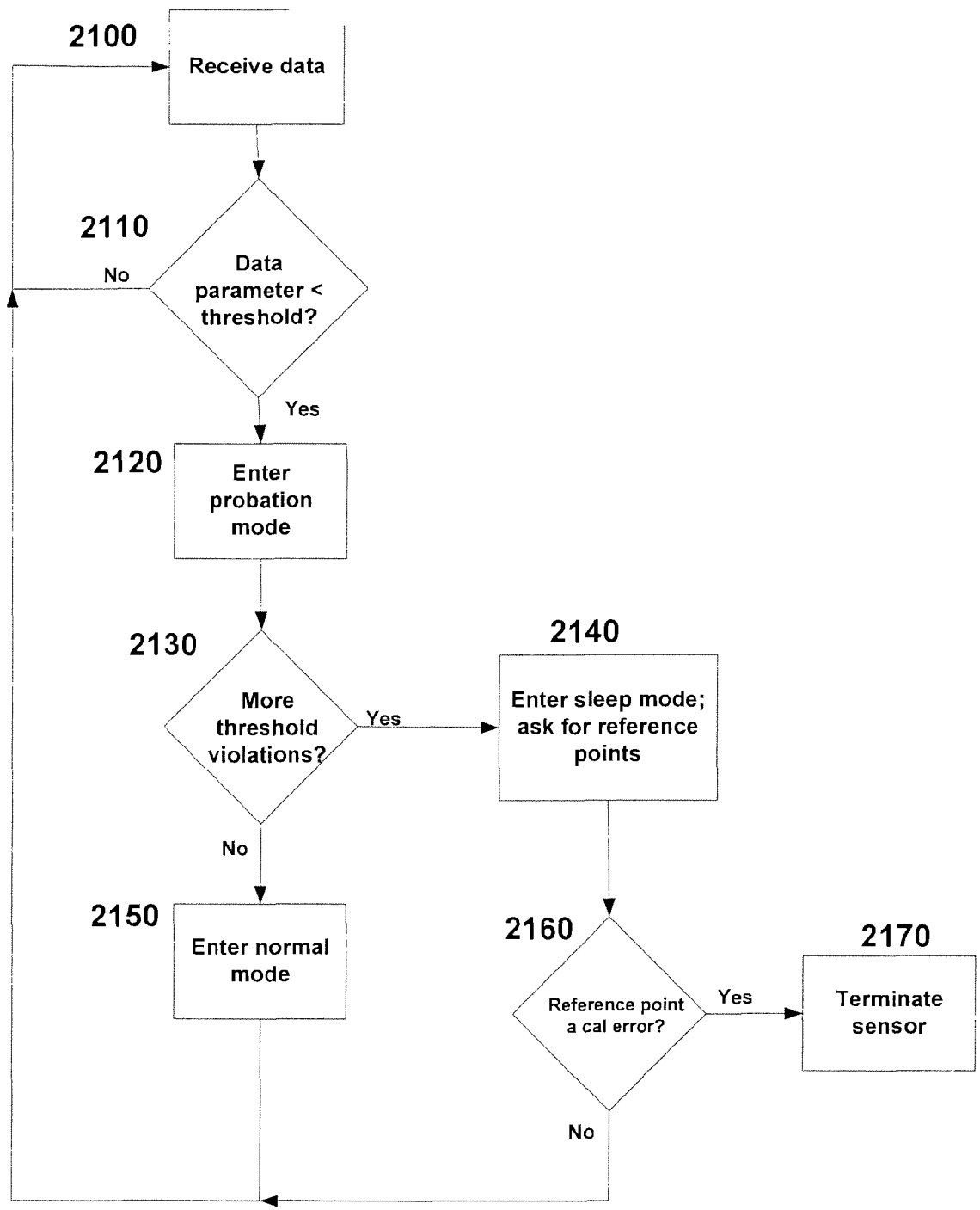
FIG. 20 shows a detailed flow diagram for implementing verification of data integrity according to an embodiment of the present invention.

FIG. 20 shows a detailed flow diagram for implementing verification of data integrity according to an embodiment of the present invention. At step 2100, ISIG values are received from a sensor, such as the glucose sensor 12, for example. The ISIG values may be received continuously or at periodic intervals. At this point, the sensor is in a first mode, such as, for example, a "normal" mode.

At step 2110, the ISIG values or a parameter related to the ISIG values are compared to a predetermined threshold. For example, according to an embodiment of the present invention, the second-order derivative of the ISIG values may be compared to a predetermined threshold, where the predetermined threshold is based on empirical studies of insulin/glucose response and varies based on the sensitivity of the sensor itself. Generally, the second-order derivative defines the acceleration of blood glucose concentration in a patient. An abnormal drop of apparent blood glucose concentration in a patient may indicate a sudden sensor low current behavior or a high amplitude noise condition. According to an embodiment of the present invention, the second-order derivative may be derived using a 5-point, third order polynomial fit.

In addition, according to an embodiment of the present invention, a first-order derivative may also be compared against a predetermined threshold. The first-order derivative is typically an indication that a patient's blood glucose is changing at a particular rate. The first-order derivative defines the rate of change of glucose concentration and can also be able to indicate sensor abnormalities. According to an embodiment of the present invention, the first-order derivative calculation can be based on the final glucose value reading rather than the ISIG values themselves. However, in alternative embodiments, the first-order derivative may use ISIG values rather than the final sensor readings or the second-order derivative may use the final sensor readings rather than ISIG values. In other words, because the ISIG values are directly related to the final sensor readings, the first-order or second-order derivatives calculations can be derived from any data points as long as the thresholds are adequately adjusted.

The predetermined threshold may vary depending on the current level of blood glucose in the patient. The threshold may be a function of the current level of blood glucose in the patient. At higher glucose levels, the glucose level may potentially change at a faster rate than at lower glucose levels. Thus, at higher glucose levels the threshold may be more negative than it is at lower glucose levels.

According to an embodiment of the present invention, if the ISIG values or a parameter related to the ISIG values do not exceed a predetermined threshold, the sensor remains in the first mode and data that is received continues to pass through an integrity verification. At step 2110, if the ISIG values or a parameter related to the ISIG values exceed a predetermined threshold, or, for example, if a combination of ISIG values or a parameter related to the ISIG values exceed predetermined thresholds, the sensor enters a second mode, such as, for example, a "probation" mode at step 2120, during which time data may be monitored for additional threshold violations and, if additional threshold violations are found, action may be taken. In further embodiments, step 2110 can require just a single trigger, a certain combination of triggers, or multiple triggers. Thus, for example, step 2110 can do a first integrity check (i.e. the second-order derivative against a first threshold) or a second integrity check (first-order derivative against a second threshold) or both integrity checks. In addition, the "probation" mode can be triggered at step 2120 based on just one integrity check failure or require any or all of the integrity checks to fail.

At step 2130, additional threshold violations may be monitored for subsequent ISIGs or sensor glucose values received from the sensor. For example, according to an embodiment of the present invention, if a second-order derivative of an ISIG value is less than a predetermined threshold, the sensor enters a probation mode. Once the sensor enters a probation mode, if another second-order derivative of an ISIG value exceed a predetermined threshold within a predefined period of time, such as one hour, for example, the sensor may enter a third mode at step 2140. If no other second-order derivative of an ISIG value exceed a predetermined threshold within the predefined period of time, the data violating the predetermined threshold may be discarded and the sensor may return to the first mode of operation and receipt of data and threshold comparisons may continue.

At step 2140, the sensor has entered a third mode, such as a "sleep" mode, for example, during which time the glucose display is turned off. A variety of conditions may send the sensor into the third mode. For example, in addition to the aforementioned condition of two integrity check failures within one hour, the sensor may enter the sleep mode if one integrity check failure is received followed by a rapid drop of the blood glucose concentration in the patient. A rapid drop of the blood glucose concentration in the patient may be defined by a first-order derivative. For example, according to an embodiment of the present invention, a rapid drop of the blood glucose concentration in the patient is assumed if the first-order derivative of the blood glucose concentration is less than −80 mg/dl/min. Also, when Isig is below 10 nA and the first-order derivative is less than a given threshold, the integrity check may trigger a new reference point. The first-order derivative of the blood glucose concentration may be derived in a variety of ways. For example, according to an embodiment of the present invention, the first-order derivative may be derived using a 5-point, second-order polynomial fit.

Other conditions may also send the sensor into the third mode. For example, according to another embodiment of the present invention, two consecutive calibration errors may also send the sensor into the third mode of operation.

At step 2160, a determination is made on whether the sensor should return to normal operation or be terminated. A return to normal operation may be made after a predefined period of time or other criteria. In any event, in order for the sensor to return to normal operation, a reference point is needed. Thus, the system prompts the patient for a blood glucose reading, i.e., the patient must perform a "finger stick" procedure during which the patient extracts a sample of his or her blood and measures the glucose concentration in the blood. If it is determined that the blood glucose measurement is not a calibration error, the sensor returns to normal operation. If it is determined that the blood glucose measurement is a calibration error, the sensor is terminated at step 2170.

Figure 21A:
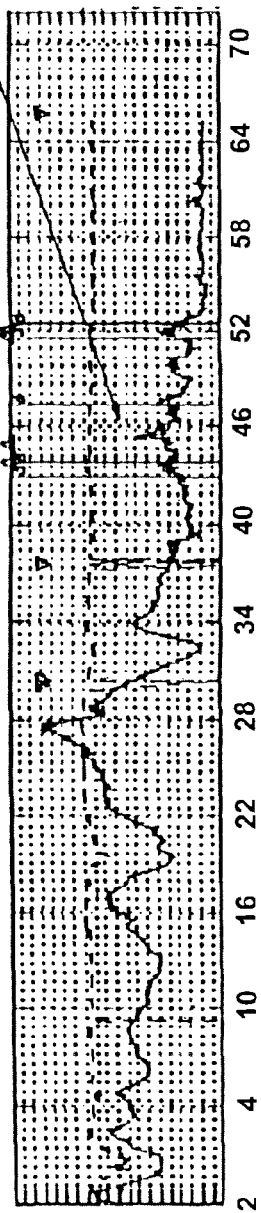
FIGS. 21a-21d show graphs of a sensor current, a first-order derivative of the sensor current, a second-order derivative of the sensor current, and a calculated sensor signal, respectively, according to an embodiment of the present invention.
Figure 21B:
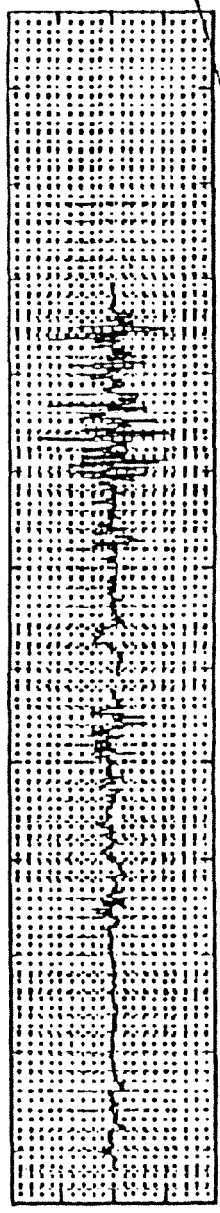
Figure 21C:
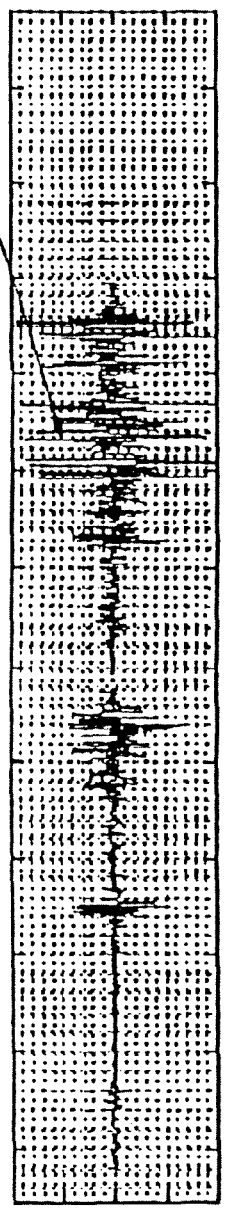
Figure 21D:
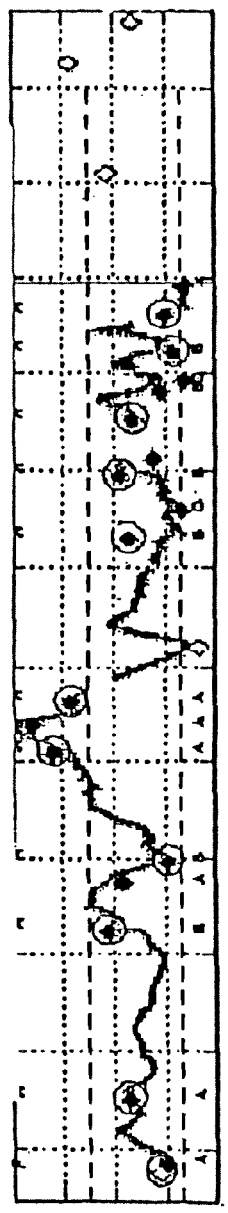

FIGS. 21a-21d show graphs of a sensor current, a first-order derivative of the sensor current, a second-order derivative of the sensor current, and a calculated sensor signal, respectively. In FIG. 21a, a noisy sensor signal 2200 may be seen. In FIG. 21c, the corresponding high amplitude second-order derivative 2210 may be seen.

A variety of filter types may be used to filter the data. Many sensor filters are linear and non-adaptive in nature and suppress noise in a particular frequency band, such that the magnitude at each frequency is suppressed by a fixed percentage regardless of amplitude. Other filters are adaptive in nature and filter signals depending on the degree or variance of noise disturbance from the environment that is convoluted with the signal of interest. Because there is a trade-off between the amount of filtering and the amount of delay introduced into a filtered signal, an adaptive filter may attenuate the amount of filtering to reduce the delay when the raw signal requires no additional filtering.

According to embodiments of the present invention, if an adaptive filter, such as a Kalman filter, for example, is used to filter ISIG values, an adequate quantifier of the variance of measurement error in the ISIG values may be desired. The quantifier may be used as an input to the adaptive filter.

The quantifier may be derived in a variety of ways. For example, noisy sensors or sensors that are no longer functioning may have similar measurement signatures which can be measured using a form of the standard deviation of a brief history of the difference of consecutive data points. According to an embodiment of the present invention, a windowed, unweighted standard deviation of the absolute value of the difference of consecutive data points may be used to derive the quantifier. For example, the quantifier $R_k$ may be determined according to the following equation:

$$R_k = c * \delta_k + b$$

where c and b are constants and $R_k$ is the estimate of the variance of noise in the raw signal at the $k^{th}$ discrete time interval. The c and b constants can be adjusted optimally to smooth the raw signal and to minimize delays. The term $\delta k$ may be calculated as follows:

$$\delta_k = \frac{\sum_{i=k-l}^{k}\left(|s_i - s_{i-1}| - \frac{\sum_{i=k-l}^{k}|s_i - s_{i-1}|}{l+1}\right)^2}{l}$$

where $s_k$ is the raw signal sampled at the $k^{th}$ discrete time interval and l is the window size of the history of consecutive differences of the raw signal.

According to another embodiment of the present invention, a recursive, weighted standard deviation of the absolute value of the difference of consecutive data points may be used to derive the quantifier. For example, the quantifier $R_k$ may be determined, as before, according to the following equation:

$$R_k = c * \delta k + b$$

where the term $\delta_k$ may be calculated as follows:

$$\delta_k = \frac{\sum\left(\alpha_k * \left(|s_k - s_{k-1}| - \frac{\sum(\alpha_k * |s_k - s_{k-1}|)}{\sum \alpha_k}\right)^2\right)}{\sum \alpha_k - 1}$$

where $s_k$ is the raw signal sampled at the $k^{th}$ discrete time interval, $\alpha_k$ is the growing exponential weight: $\alpha_k = e^{((k*\Delta t/60)/\tau)}$, $\tau$ is the exponential time constant in hours and $\Delta t$ is the sampling time in minutes.

According to an embodiment of the present invention, the recursive procedure may be performed as follows. With $\Phi = e^{((\Delta t/60)/\tau)}$, $\Sigma\alpha=0$, $\Sigma\beta=0$, $\Sigma\gamma=0$, and $\alpha=1$, then, for k=2:N:
$\alpha = \Phi * \alpha$;
$\Sigma\alpha = \Sigma\alpha + \alpha$;
$D = |s_k - s_{k-1}|$;
$\beta = \alpha * D$;
$\Sigma\beta = \Sigma\beta + \beta$;
$\gamma = \alpha * (D - \Sigma\beta/\Sigma\alpha)^2$;
$\Sigma\gamma = \Sigma\gamma + \gamma$;
$\delta_k = \Sigma\gamma/[\Sigma\alpha - 1]$;
$R_k = c * \delta_k + b$ Thus, one of the above formulations may be used to obtain an estimated variance of noise, $R_k$, on a raw signal. Once $R_k$ is obtained, it may be used as an input to an adaptive filter. The adaptive filter may then smooth out raw signal data to a degree necessary according to the magnitude of $R_k$.

Figure 22:
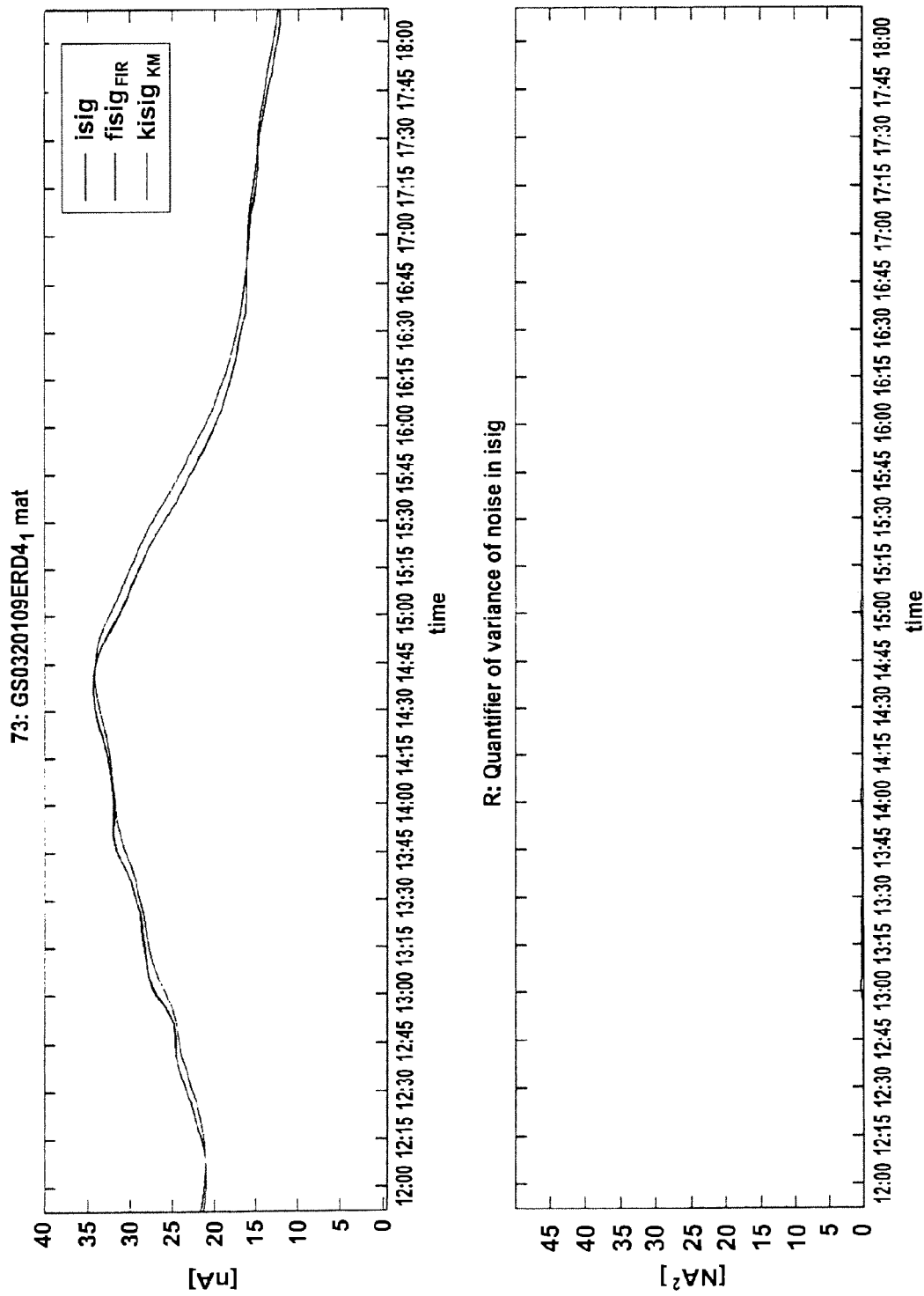
FIG. 22 is a graph illustrating how a quantifier smoothes out raw signal data according to an embodiment of the present invention.
Figure 23:
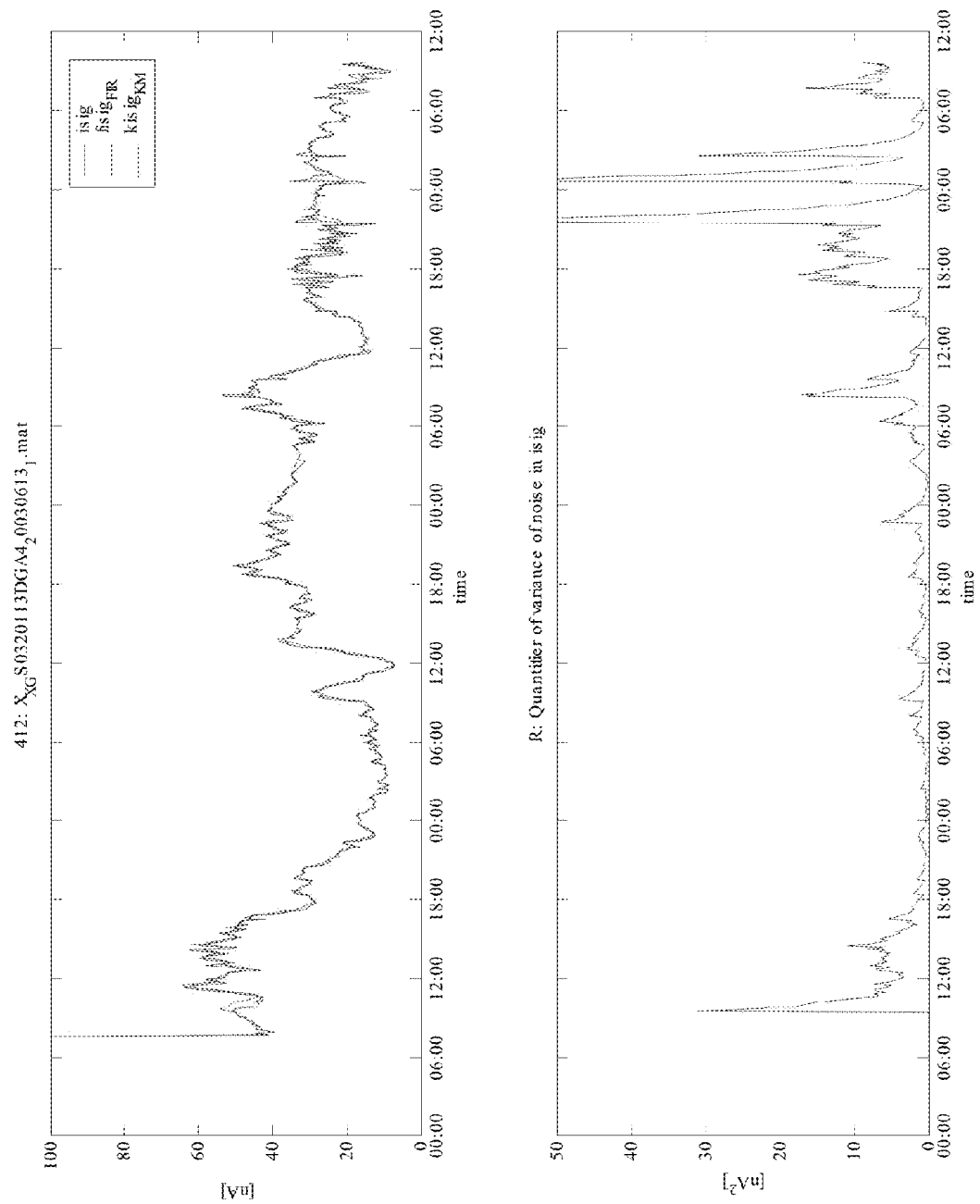
FIG. 23 is a graph illustrating how a quantifier smoothes out the raw signal data according to an embodiment of the present invention.

FIGS. 22 and 23 illustrate how the quantifier $R_k$ smoothes out the raw signal data. In FIGS. 22 and 23, "isig" represents a raw data signal, "fisig$_{FIR}$" represents a raw signal filtered with a Finite Impulse response (FIR) filter, and "kisig$_{KM}$" represents a raw signal filtered with an adaptive filter, in the embodiment shown a Kalman filter, with the quantifier $R_k$ as an input to the adaptive filter. Specifically, FIG. 22 represents a low $R_k$, where almost no filtering and minimal delay of the signal occurs because the calculated R (quantifier) is very low. FIG. 23 shows the mixture of different degrees of filtering due to changes in $R_k$. Both FIGS. 22 and 23 show the benefit of the adaptive filter method over typical FIR filtering.

Therefore, while the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A method for filtering signals from a sensor comprising:
   receiving a plurality of signal values from the sensor generated in response to a concentration of a substance;
   at a processor, computing a quantifier of a variance of a measurement error based, at least in part, on a standard deviation of an absolute value of consecutive data points within the plurality of signal values; and
   at said processor, filtering the plurality of signal values with an adaptive filter, wherein the quantifier is an input to the adaptive filter.

2. The method of claim 1, where the sensor comprises a glucose sensor.

3. The method of claim 2, wherein the plurality of data values are responsive to blood glucose concentrations.

4. The method of claim 1, wherein formulating the standard deviation comprises formulating a windowed, unweighted standard deviation.

5. The method of claim 4, wherein the quantifier is equal to $$R_k = c * \delta_k + b,$$

where $$\delta_k = \frac{\sum_{i=k-l}^{k}\left(|s_i - s_{i-1}| - \frac{\sum_{i=k-l}^{k}|s_i - s_{i-1}|}{l+1}\right)^2}{l},$$

$s_k$ is a raw signal sampled at a $k^{th}$ discrete time interval and l is a window size of a history consecutive differences of the raw signal, and wherein c and b are constants.

6. The method of claim 1, wherein the standard deviation is formulated as a recursive, weighted standard deviation.

7. The method of claim 6, wherein the quantifier is equal to $$R_k = c * \delta_k + b,$$

where $$\delta_k = \frac{\sum\left(\alpha_k * \left(|s_k - s_{k-1}| - \frac{\sum(\alpha_k * |s_k - s_{k-1}|)}{\sum \alpha_k}\right)^2\right)}{\sum \alpha_k - 1},$$

$s_k$ is a raw signal sampled at a $k^{th}$ discrete time interval, $\alpha_k$ is a growing exponential weight: $\alpha_k = e^{((k*\Delta t/60)/\tau)}$, $\tau$ is an exponential time constant in hours and $\Delta t$ is a sampling time in minutes, and wherein c and b are constants.

8. The method of claim 1, wherein the adaptive filter comprises a Kalman filter.

9. A method for calibrating a sensor comprising:
receiving a plurality of signal values from the sensor generated in response to a concentration of a substance;
computing, at a processor, a reliability metric for each signal value of the plurality of data values based, at least in part, on a standard deviation of an absolute value of consecutive data points within the plurality of signal values;
selectively discarding each of one or more of the signal values of the plurality of signal values in response to application of a threshold value to said reliability metric for the signal value;
filtering, at said processor, the signal values of the plurality of signal values that have not been discarded using an adaptive filter; and
adjusting an output of the sensor using the filtered signal values.

10. A method for calibrating a sensor comprising:
receiving a plurality of signal values from the sensor responsive to a concentration of a substance;
computing, at a processor, a reliability of each signal value of the plurality of signal values;
selectively discarding each of one Or more of the signal values of the plurality of signal values in response to application of a threshold value to said computed reliability metric for the signal;
filtering, at said processor, the signal values of the plurality of signal values that have not been discarded; and
adjusting an output of the sensor using the filtered signal values;
wherein filtering the signal values comprises filtering the signal values with an adaptive filter;
wherein filtering the signal values with an adaptive filter comprises using the adaptive filter with a parameter based, at least in part, on the signal values of the plurality of signal values that have not been discarded; and
wherein the parameter is representative of a standard deviation of the signal values of the plurality of signal values that have not been discarded or is representative of a standard deviation of an absolute value of signal values within the signal values of the plurality of signal values that have not been discarded.

11. The method of claim 10, wherein the standard deviation comprises a windowed, unweighted standard deviation.

12. The method of claim 10, wherein the standard deviation comprises a recursive, weighted standard deviation.

13. An apparatus for filtering signal values from a sensor comprising:
means, comprising a processor, for receiving a plurality of signal values from the sensor;
means, comprising said processor, for Obtaining a quantifier of a variance of a measurement error associated with the plurality of signal values based, at least in part, on a standard deviation of an absolute value of consecutive data points within the plurality of signal values; and
means, comprising said processor, for filtering the plurality of signal values with an adaptive filter, wherein the quantifier is an input value to the adaptive filter.

14. The apparatus of claim 13, where the sensor comprises a glucose sensor.

15. The apparatus of claim 14, wherein the plurality of signal ues are generated by said sensor in response to blood glucose concentrations.

16. The apparatus of claim 13, wherein said means for obtaining a quantifier comprises means for formulating a standard deviation of an absolute value of consecutive signal values within the plurality of signal values.

17. The apparatus of claim 16, wherein said means for formulating the standard deviation comprises means for formulating a windowed, unweighted standard deviation.

18. The apparatus of claim 16, wherein said means for formulating the standard deviation comprises means for formulating a recursive, weighted standard deviation.

19. The apparatus of claim 13, wherein the adaptive filter comprises a Kalman filter.

20. The method of claim 9, wherein the adaptive filter comprises a Kalman filter.

* * * * *